(12) United States Patent
LaVon et al.

(10) Patent No.: US 8,257,335 B2
(45) Date of Patent: Sep. 4, 2012

(54) DIAPER HAVING HIP STRETCH PANELS

(75) Inventors: Gary Dean LaVon, Liberty Township, OH (US); Kevin Michael Smith, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 771 days.

(21) Appl. No.: 11/700,585

(22) Filed: Jan. 31, 2007

(65) Prior Publication Data

US 2008/0183149 A1     Jul. 31, 2008

(51) Int. Cl.
*A61F 13/15*     (2006.01)
(52) U.S. Cl. .................. 604/394; 604/386; 604/402
(58) Field of Classification Search .......... 604/393, 604/394, 402
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |

(Continued)

FOREIGN PATENT DOCUMENTS

EP     0 206 208     12/1986

(Continued)

OTHER PUBLICATIONS

PCT International Search Report, PCT/IB2008/050285 dated Jan. 31, 2007.

*Primary Examiner* — Melanie Hand
(74) *Attorney, Agent, or Firm* — Richard L. Alexander

(57) ABSTRACT

A disposable absorbent article including a chassis and an absorbent assembly in combination with a support element that extends circumferentially around the waist of the wearer. The support element includes hip stretch panels. The chassis includes a water-impermeable backsheet that may be folded laterally inward at both of its side edges to form opposing side flaps. Each side flap is attached to the interior surface of the chassis adjacent to its end edges. Each side flap has a longitudinally extending elastic gathering member attached adjacent to its proximal edge. The chassis may include an extensible formed web material. The absorbent assembly may be attached in a cruciform pattern to the chassis to allow unattached portions of the chassis to extend laterally. Frangible tear lines and/or tear locator lines may be formed to facilitate removal of the article from the wearer.

14 Claims, 13 Drawing Sheets

U.S. PATENT DOCUMENTS

| | | |
|---|---|---|
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,592,194 A | 7/1971 | Duncan |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,585,450 A | 4/1986 | Rosch et al. |
| 4,589,878 A | 5/1986 | Mitrani |
| 4,601,717 A | 7/1986 | Blevins |
| 4,610,678 A | 9/1986 | Weisman et al. |
| 4,636,207 A | 1/1987 | Buell |
| 4,670,011 A | 6/1987 | Mesek |
| 4,680,030 A | 7/1987 | Coates et al. |
| 4,681,581 A | 7/1987 | Coates |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A * | 7/1990 | Van Gompel et al. ......... 604/396 |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,476,458 A | 12/1995 | Glaug et al. |
| 5,518,801 A | 5/1996 | Chappell et al. |
| 5,531,730 A | 7/1996 | Dreier |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,622,589 A | 4/1997 | Johnson et al. |
| 5,624,424 A | 4/1997 | Saisaka et al. |
| 5,625,222 A | 4/1997 | Yoneda et al. |
| 5,626,571 A | 5/1997 | Young et al. |
| 5,635,191 A | 6/1997 | Roe et al. |
| 5,643,243 A | 7/1997 | Klemp |
| 5,643,588 A | 7/1997 | Roe et al. |
| H1674 H | 8/1997 | Ames et al. |
| 5,662,638 A | 9/1997 | Johnson et al. |
| 5,674,215 A | 10/1997 | Ronnberg |
| 5,691,035 A | 11/1997 | Chappell et al. |
| 5,723,087 A | 3/1998 | Chappell et al. |
| 5,749,866 A | 5/1998 | Roe et al. |
| 5,752,947 A | 5/1998 | Awolin |
| 5,772,825 A | 6/1998 | Schmitz |
| 5,776,121 A | 7/1998 | Roe et al. |
| 5,779,831 A | 7/1998 | Schmitz |
| 5,797,894 A | 8/1998 | Cadieux et al. |
| 5,810,800 A | 9/1998 | Hunter et al. |
| 5,814,035 A | 9/1998 | Gryskiewicz et al. |
| 5,846,232 A | 12/1998 | Serbiak et al. |
| 5,851,204 A | 12/1998 | Mizutani |
| 5,853,402 A | 12/1998 | Faulks et al. |
| 5,865,823 A | 2/1999 | Curro |
| 5,873,868 A | 2/1999 | Nakahata |
| 5,876,391 A | 3/1999 | Roe et al. |
| 5,891,544 A | 4/1999 | Chappell et al. |

| | | |
|---|---|---|
| 5,897,545 A | 4/1999 | Kline et al. |
| 5,904,673 A | 5/1999 | Roe et al. |
| 5,931,825 A | 8/1999 | Kuen et al. |
| 5,951,536 A | 9/1999 | Osborn, III et al. |
| 5,957,908 A | 9/1999 | Kline et al. |
| 5,968,029 A | 10/1999 | Chappell et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,102,892 A | 8/2000 | Putzer et al. |
| 6,107,537 A | 8/2000 | Elder et al. |
| 6,110,157 A | 8/2000 | Schmidt |
| 6,117,121 A | 9/2000 | Faulks et al. |
| 6,120,486 A | 9/2000 | Toyoda et al. |
| 6,120,487 A | 9/2000 | Ashton |
| 6,120,489 A | 9/2000 | Johnson et al. |
| 6,120,632 A * | 9/2000 | Dragoo et al. ............... 156/164 |
| 6,120,866 A | 9/2000 | Arakawa et al. |
| 6,129,720 A | 10/2000 | Blenke et al. |
| 6,156,424 A | 12/2000 | Taylor |
| 6,165,160 A | 12/2000 | Suzuki et al. |
| 6,174,302 B1 | 1/2001 | Kumasaka |
| 6,177,607 B1 | 1/2001 | Blaney et al. |
| 6,186,996 B1 | 2/2001 | Martin |
| 6,210,390 B1 | 4/2001 | Karlsson |
| 6,238,380 B1 | 5/2001 | Sasaki |
| 6,241,716 B1 | 6/2001 | Rönnberg |
| 6,312,420 B1 | 11/2001 | Sasaki et al. |
| 6,322,552 B1 | 11/2001 | Blenke et al. |
| 6,325,787 B1 | 12/2001 | Roe et al. |
| 6,334,858 B1 | 1/2002 | Rönnberg et al. |
| 6,350,332 B1 | 2/2002 | Thomas et al. |
| 6,364,863 B1 | 4/2002 | Yamamoto et al. |
| 6,402,729 B1 | 6/2002 | Boberg et al. |
| 6,402,731 B1 | 6/2002 | Suprise et al. |
| 6,410,820 B1 | 6/2002 | McFall et al. |
| 6,413,249 B1 | 7/2002 | Turi et al. |
| 6,419,667 B1 | 7/2002 | Avalon et al. |
| 6,432,098 B1 | 8/2002 | Kline et al. |
| 6,432,099 B2 | 8/2002 | Rönnberg |
| 6,443,933 B1 | 9/2002 | Suzuki et al. |
| 6,461,342 B2 | 10/2002 | Tanji et al. |
| 6,461,343 B1 | 10/2002 | Schaefer et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,520,947 B1 | 2/2003 | Tilly et al. |
| 6,524,294 B1 | 2/2003 | Hilston et al. |
| 6,585,713 B1 | 7/2003 | LeMahieu et al. |
| 6,602,234 B2 | 8/2003 | Klemp et al. |
| 6,605,070 B2 | 8/2003 | Ludwig et al. |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,682,515 B1 | 1/2004 | Mizutani et al. |
| 6,689,115 B1 | 2/2004 | Popp et al. |
| 6,716,205 B2 | 4/2004 | Popp et al. |
| 6,726,792 B1 | 4/2004 | Johnson et al. |
| 6,755,808 B2 | 6/2004 | Balogh et al. |
| 6,818,083 B2 | 11/2004 | Mcamish et al. |
| 6,880,211 B2 | 4/2005 | Jackson et al. |
| 6,923,797 B2 | 8/2005 | Shinohara et al. |
| 6,962,578 B1 | 11/2005 | LaVon |
| 6,972,010 B2 | 12/2005 | Pesce et al. |
| 6,976,978 B2 * | 12/2005 | Ruman et al. ............ 604/385.01 |
| 7,014,632 B2 | 3/2006 | Takino et al. |
| 7,037,299 B2 | 5/2006 | Turi et al. |
| 7,048,726 B2 | 5/2006 | Kusagawa et al. |
| 7,160,281 B2 * | 1/2007 | LeMinh et al. .......... 604/385.22 |
| 2002/0045881 A1 | 4/2002 | Kusibojoska et al. |
| 2002/0099351 A1 | 7/2002 | Onishi et al. |
| 2002/0173767 A1 | 11/2002 | Popp et al. |
| 2003/0088223 A1 | 5/2003 | Vogt et al. |
| 2003/0144644 A1 | 7/2003 | Murai et al. |
| 2003/0148694 A1 | 8/2003 | Ghiam |
| 2003/0233082 A1 | 12/2003 | Kline et al. |
| 2004/0022998 A1 | 2/2004 | Miyamoto et al. |
| 2004/0082928 A1 | 4/2004 | Pesce et al. |
| 2004/0122411 A1 | 6/2004 | Hancock-Cooke |
| 2004/0147890 A1 * | 7/2004 | Nakahata et al. ........ 604/385.01 |
| 2004/0162536 A1 | 8/2004 | Becker et al. |
| 2004/0167486 A1 | 8/2004 | Busam et al. |
| 2004/0186456 A1 | 9/2004 | Nawata et al. |
| 2004/0225271 A1 | 11/2004 | Datta et al. |
| 2004/0236299 A1 | 11/2004 | Tsang et al. |
| 2004/0236304 A1 | 11/2004 | Coates et al. |
| 2004/0249355 A1 | 12/2004 | Tanio et al. |
| 2005/0004548 A1 | 1/2005 | Otsubo et al. |
| 2005/0038401 A1 | 2/2005 | Suzuki et al. |
| 2005/0085784 A1 | 4/2005 | LeMinh et al. |
| 2005/0131373 A1 | 6/2005 | Wright et al. |
| 2005/0171499 A1 | 8/2005 | Nigam et al. |
| 2005/0203475 A1 | 9/2005 | LaVon et al. |
| 2005/0203479 A1 | 9/2005 | Sakaguchi et al. |
| 2005/0288645 A1 | 12/2005 | LaVon |
| 2005/0288646 A1 | 12/2005 | LaVon |
| 2006/0135936 A1 | 6/2006 | Markovich et al. |
| 2006/0264860 A1 | 11/2006 | Beck |
| 2006/0264861 A1 | 11/2006 | LaVon et al. |

FOREIGN PATENT DOCUMENTS

| | | |
|---|---|---|
| EP | 0 403 832 A1 | 12/1990 |
| EP | 0 893 115 | 1/1999 |
| EP | 0 916 327 A1 | 5/1999 |
| ES | 2 213 491 A1 | 8/2004 |
| FR | 2 566 631 A1 | 1/1986 |
| FR | 2 612 770 A1 | 9/1988 |
| FR | 2 810 234 | 12/2001 |
| GB | 1 513 055 | 6/1978 |
| GB | 2 101 468 | 1/1983 |
| GB | 2 262 873 A | 7/1993 |
| JP | 04 122256 | 4/1992 |
| JP | 11-318980 | 11/1999 |
| WO | WO 95/16746 A1 | 6/1995 |
| WO | WO 95/29657 | 11/1995 |
| WO | WO 98/16179 A1 | 4/1998 |
| WO | WO 99/13813 | 3/1999 |
| WO | WO 2004/105664 | 12/2004 |
| WO | WO 2006/123976 | 11/2006 |
| WO | WO 2007/000315 | 1/2007 |

* cited by examiner

DIAPER HAVING HIP STRETCH PANELS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact. As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A disposable absorbent article includes a chassis and an absorbent assembly in combination with a support element that extends circumferentially around the waist of the wearer. The support element includes hip stretch panels. The chassis includes a water-impermeable backsheet that may be folded laterally inward at both of its side edges to form opposing side flaps. Each side flap is attached to the interior surface of the chassis adjacent to its end edges. Each side flap has a longitudinally extending elastic gathering member attached adjacent to its proximal edge. The chassis may include an extensible formed web material. The absorbent assembly may be attached in a cruciform pattern to the chassis to allow unattached portions of the chassis to extend laterally.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., left and right symmetric elements may be respectively identified by the reference numerals 1a and 1b. A reference numeral without an appended lowercase letter identifies all of the elements to which that particular reference numeral applies, e.g., the same elements as a group may be designated 1.

In FIG. 1, the interior of the diaper is shown facing the viewer.

DETAILED DESCRIPTION OF THE INVENTION

Figure 1:
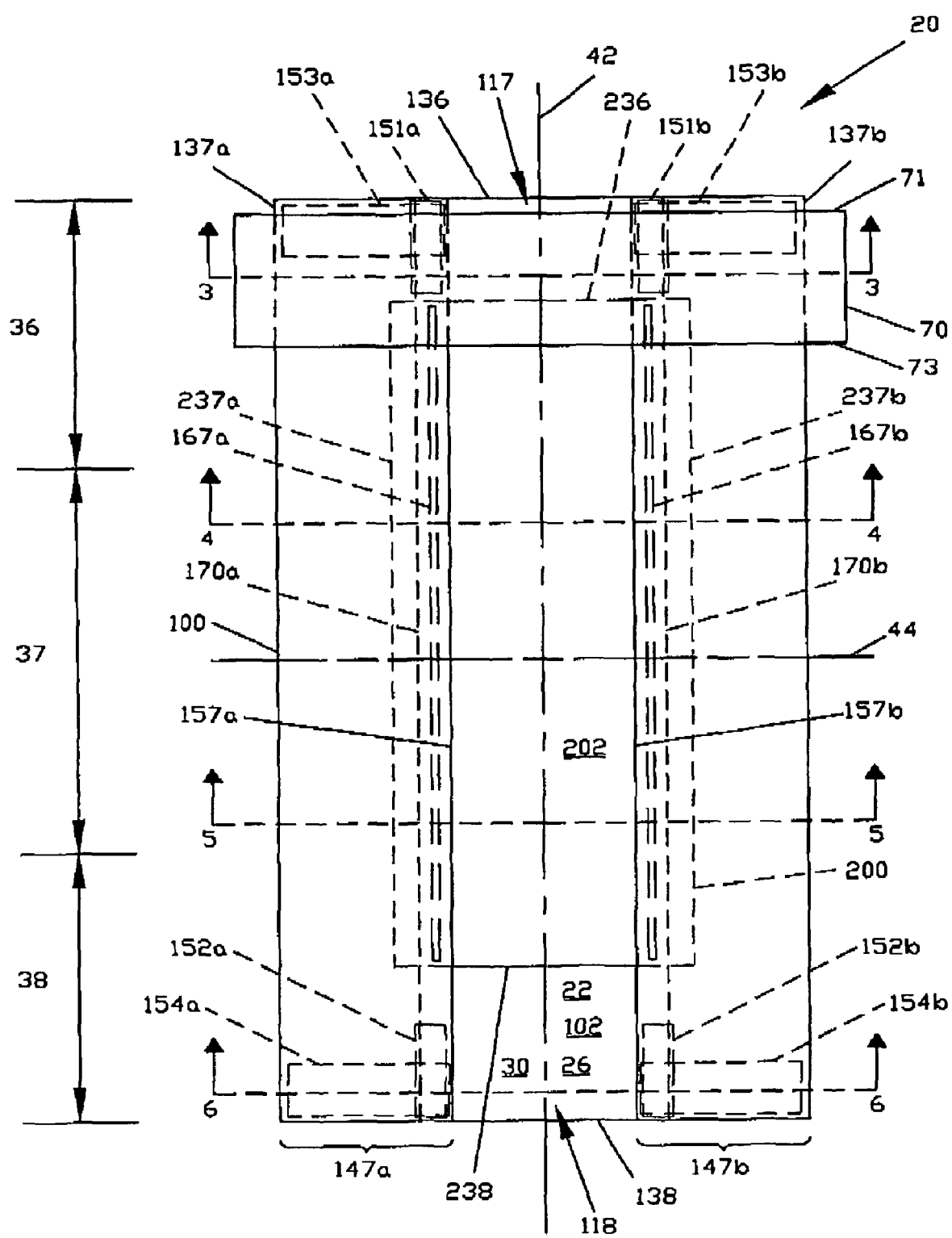
FIG. 1 is a plan view of an exemplary disposable absorbent article in the form of a diaper 20, which is shown in its flat, uncontracted state, i.e., without the contraction induced by elastic members, with a support element 70 attached to the front waist region 36, prior to the attachment of the support element 70 to the back waist region 38.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45° of the longitudinal direction are considered to be "longitudinal".

The term "lateral" refers to a direction running from a side edge to an opposing side edge of the article and generally at a right angle to the longitudinal direction. Directions within 45° of the lateral direction are considered to be "lateral".

The term "circumferential" refers to a direction generally encircling the waist of the wearer parallel to the lateral direction. This term is used particularly when describing the support element, which extends all the way around the waist opening, rather than only from one side edge to the opposing side edge of the article.

The term "disposed" refers to an element being attached and positioned in a particular place or position in a unitary structure with other elements.

The term "attach" refers to elements being connected or united by adhering, bonding, etc., by any method suitable for the elements being attached together and their constituent materials. Many suitable methods for attaching elements together are well-known, including adhesive bonding, pressure bonding, thermal bonding, etc. Such attachment methods may be used to attach elements together over a particular area either continuously or intermittently. Unless indicated otherwise, elements that are described as being attached to each other are attached directly together, with either nothing or only bonding material, e.g., an adhesive, between them. Unless indicated otherwise, elements that are described as being attached to each other are attached permanently together, i.e., attached in such a way that one or both of the elements and/or any bonding material that is present must be damaged in order to separate them. This permanent attachment excludes temporary attachment, such as fastening elements together by means of fasteners that may be unfastened.

The term "laminate" refers to elements being attached together in a layered arrangement.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "proximal" and "distal" refer respectively to the location of an element near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

The term "nonwoven" refers to a sheet, web, or batt of directionally or randomly oriented fibers, made by bonding or entangling the fibers through mechanical, thermal, or chemical means. Nonwoven materials exclude paper and products which are woven, knitted, tufted, or felted by wet milling. The fibers are preferably but not necessarily man-made synthetics.

In the following description and in the drawing figures, various structural elements are identified by reference numerals without suffixed letters when referring to the group as a whole and by the same reference numerals with suffixed letters when distinguishing between, for example, left and right members of the group. As an example, the side flaps as a group are identified by the reference numeral 147 while the individual left and right side flaps are respectively designated as elements 147a and 147b.

Description of Exemplary Diaper Embodiment

In FIG. 1, FIG. 2, FIG. 3, FIG. 4, FIG. 5, and FIG. 6, the exemplary diaper 20 is shown in its flat uncontracted state prior to being formed into a pant. The finished pant product is shown in FIG. 7, FIG. 8, FIG. 9, and FIG. 10.

One end portion of the exemplary diaper 20 is configured as a front waist region 36. The longitudinally opposing end portion is configured as a back waist region 38. An intermediate portion of the diaper 20 extending longitudinally between the front waist region 36 and the back waist region 38 is configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138. The lateral axis 44 extends through the midpoint of the left side edge 137a and through the midpoint of the right side edge 137b. The exemplary chassis 100 shown in FIG. 1 additionally has longitudinally extending and laterally opposing side flaps 147a and 147b that are described in more detail below.

The basic structure of the diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237a, and right side edge 237b of the absorbent assembly 200 may lie inward of the respective front waist edge 136, back waist edge 138, left side edge 137a, and right side edge 137b of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

The basic structure of the diaper 20 also includes a support element 70 that is attached to the interior surface 102 of the chassis 100. In FIG. 1, FIG. 2, FIG. 3, FIG. 4, FIG. 5, and FIG. 6, the diaper 20 is shown in its flat uncontracted state prior to being formed into a pant. Therefore, for clarity, the support element 70 is shown attached to the chassis 100 only in the front waist region 36 of the diaper 20 in these figures. In order to complete the assembly of the diaper 20 shown in these figures, the support element 70 is subsequently attached to the chassis 100 in the back waist region 38 of the diaper 20 as described below and as shown in FIG. 7, FIG. 8, FIG. 9, FIG. 10, FIG. 12, FIG. 13, FIG. 14, FIG. 15, FIG. 16, and FIG. 17. The support element 70 could have been shown attached in only the back waist region 38 in FIG. 1, FIG. 2, and FIG. 3, instead of the front waist region 36, with the same effect, i.e., the sequence in which the support element 70 is attached in the waist regions 36 and 38 is not important for the purpose of this description of the structure. The support element 70 has a circumferentially extending longitudinally distal edge 71 that is disposed adjacent to the front waist edge 136 of the chassis 100 and a longitudinally opposing circumferentially extending longitudinally proximal edge 73.

Figure 7:
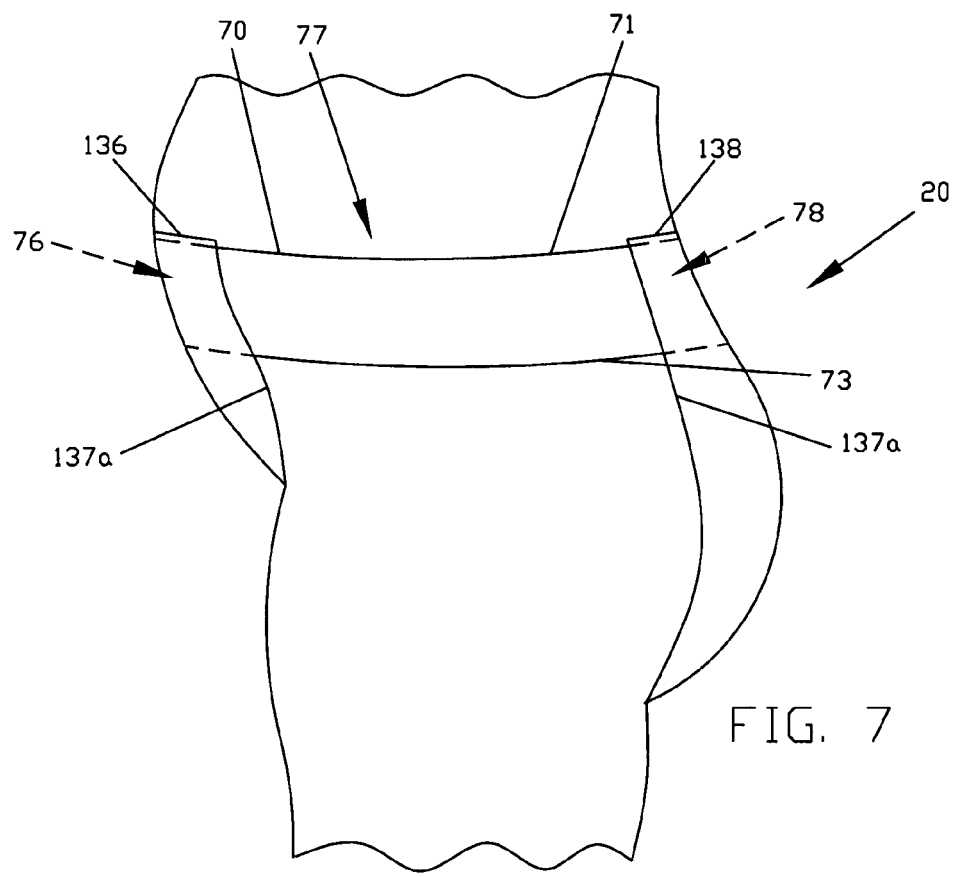
FIG. 7 is a simplified side elevation view of an exemplary diaper 20 being worn about a lower torso of a wearer.
Figure 8:
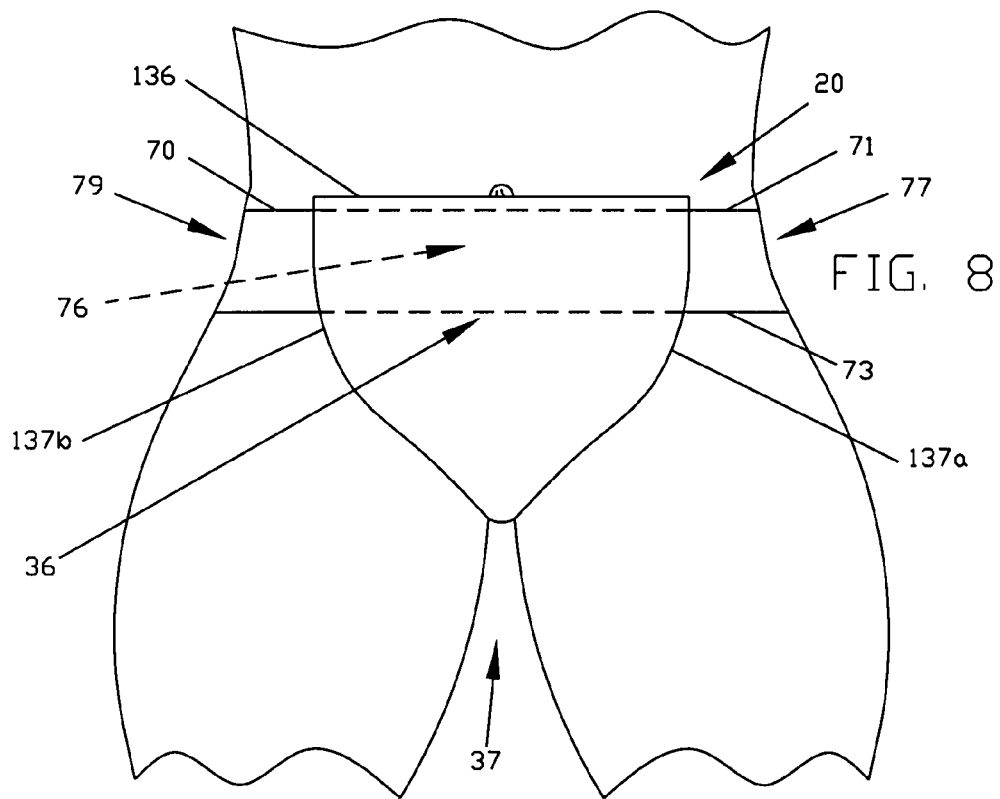
FIG. 8 is a front elevation view of the diaper 20 of FIG. 7.
Figure 9:
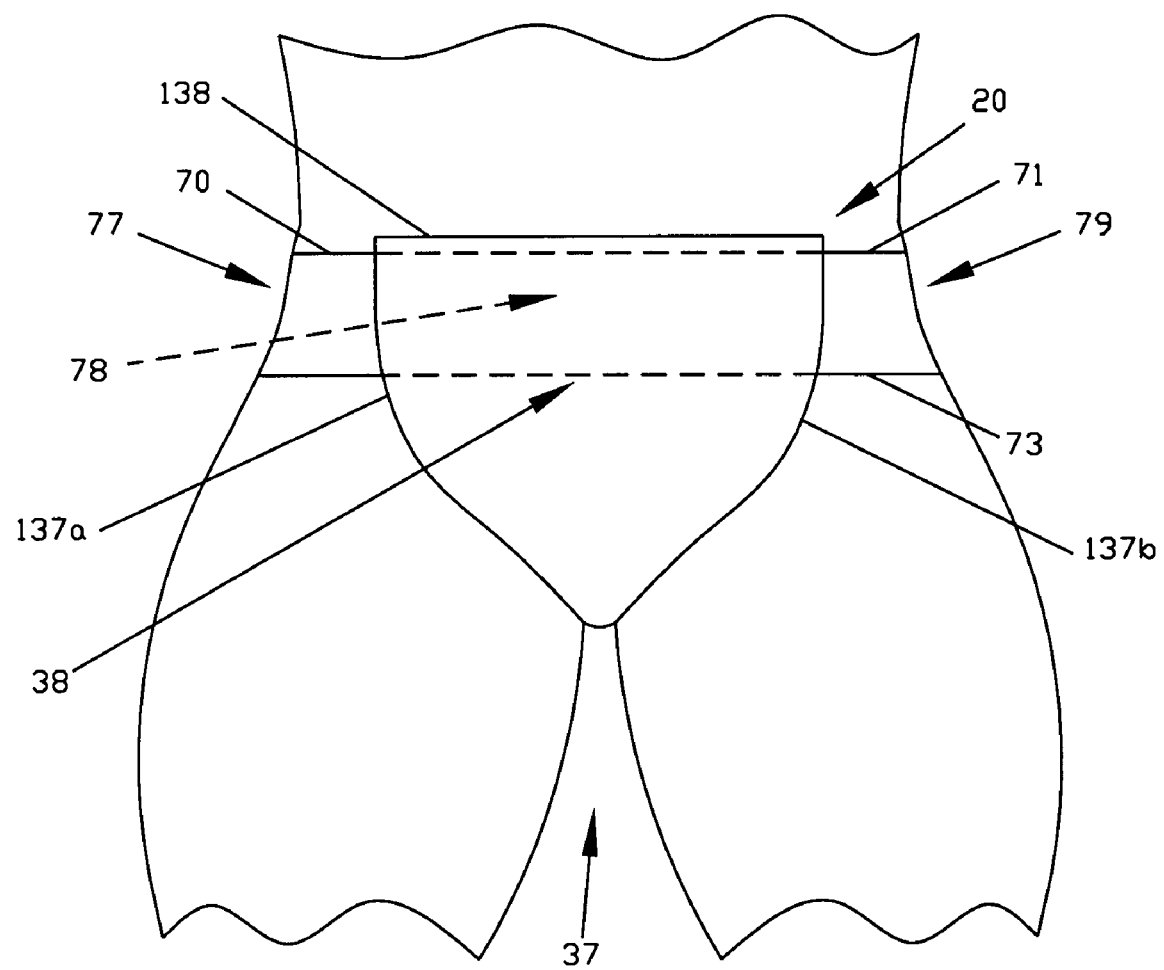
FIG. 9 is a back elevation view of the diaper 20 of FIG. 7.

As shown in FIG. 7, FIG. 8, and FIG. 9, when the diaper 20 is worn on the lower torso of a wearer, the front waist edge 136 and the back waist edge 138 of the chassis 100 in combination with the distal edge 71 of the support element 70 encircle the waist of the wearer, while at the same time the chassis side edges 137a and 137b in combination with the proximal edge 73 of the support element 70 encircle the legs of the wearer. At the same time, the crotch region 37 is generally positioned between the legs of the wearer and the absorbent assembly 200 extends from the front waist region 36 through the crotch region 37 to the back waist region 38.

Description of the Chassis

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as a laminate of a film 30 and a nonwoven material 31 or a laminate of multiple nonwoven layers, may also be suitable for use as the backsheet 26. Such a backsheets may be oriented with the nonwoven 31 disposed exteriorly of the film, as shown in FIG. 1, FIG. 2, FIG. 3, FIG. 4, FIG. 5, and FIG. 6, to provide the feel and appearance of a more cloth-like outermost layer than would be provided by using the film 30 as the outermost layer.

The chassis 100 may, but need not, additionally include an inner liner 22 attached to the backsheet 26. The inner liner 22 may form a portion of the interior surface 102 of the chassis 100 that is intended to be placed against the body of the wearer. For example, the inner liner may cover and thereby lie interiorly of a portion or all of the absorbent assembly 200. The inner liner 22 is preferably formed of a soft material that will not irritate the skin of the wearer. Such an inner liner 22 may serve to isolate the skin of the wearer from a portion of the backsheet 26 as may be desirable, for example, when the diaper 20 is worn under conditions in which contact between the skin and a backsheet film could be uncomfortable. Many suitable materials for the inner liner 22 are well-known in the art, including rayon and synthetic nonwovens such as spun-bonded or carded polypropylene or polyester or other olefinic materials. The inner liner 22 may extend to the same width and the same length as the backsheet 26. Alternatively, one or more of the edges of the inner liner 22 may lie inward of the edges of the backsheet 26.

As shown in FIG. 1, FIG. 2, FIG. 3, FIG. 4, FIG. 5, and FIG. 6, the exemplary chassis 100 has longitudinally extending and laterally opposing side flaps 147a and 147b that are disposed on the interior portion of the diaper 20 that faces inwardly toward the wearer and contacts the wearer. The side flaps 147 may be formed by folding portions of the chassis 100 laterally inward, i.e., toward the longitudinal axis 42, to form both the respective side flaps 147 and the side edges 137 of the chassis 100. Alternatively, the side flaps 147 may be formed by attaching an additional layer or layers to the chassis 100 at or adjacent to each of the respective side edges 137 of the chassis 100. In embodiments in which the side flaps are formed by attaching an additional layer or layers to the chassis, each of the additional layer or layers may be attached at or adjacent to its laterally distal edge.

Portions of a film backsheet 26 that are folded laterally inward to form the side flaps may contact the skin of a wearer during the use of the diaper 20. However, in embodiments comprising an extensible backsheet, the alternating ridges and valleys in such a film backsheet that has been deformed in order to make it extensible may provide channels through which air can pass to alleviate any concern regarding such contact of the film backsheet with the skin.

In embodiments in which portions of the chassis 100 are folded laterally inward to form the side flaps 147, the chassis 100 may simply be folded loosely or may be creased along a portion of each of its side edges 137. For example, it may be desirable to form creases along portions of the side edges 137 in the crotch region 37 in order to impart a more finished appearance to the diaper 20. Alternatively or in addition to creasing, a portion of each of the folded side flaps 147 adjacent to the side edges 137 may be attached to the interior surface 102 of the chassis 100 to achieve a similar result.

The left side flap 147a has a proximal edge 157a and the right side flap 147b has a proximal edge 157b. In the exemplary diaper 20 shown in FIG. 1, the side flaps 147 overlap the absorbent assembly 200, i.e., the proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200.

In the exemplary chassis 100 shown in FIG. 1, the side flaps 147 extend the full length of the chassis 100 between the front waist edge 136 and the back waist edge 138. Such a full length configuration may be desirable in order to minimize the amount of waste material and the difficulty associated with the manufacture of the diaper 20, especially when the method used to manufacture the diaper 20 requires the introduction of the material or materials for the chassis 100 in the form of a continuous web or multiple continuous webs. Alternatively, the side flaps may be shorter and extend less than the full distance between the front waist edge 136 and the back waist edge 138. Such a shorter configuration may be desirable in order to minimize the total amount of material used in the manufacture of the diaper 20.

Each of the side flaps 147 is attached to the interior surface 102 of the chassis 100 in attachment zones located in the front waist region 36 and in the back waist region 38. For example, in the chassis 100 shown in FIG. 1, the side flaps 147 are attached to the interior surface 102 of the chassis 100 in the attachment zones 151. These longitudinally oriented attachment zones may have equal areas or may be unequal in area. For example, the front longitudinally oriented attachment zones 151 may be of one size and the back longitudinally oriented attachment zones 152 may be of another size.

In the exemplary chassis 100 shown in FIG. 1, the side flaps 147 are also attached to the interior surface 102 of the chassis 100 in laterally oriented attachment zones 153 adjacent to the front waist edge 136 and in a longitudinally opposing laterally oriented attachment zones 154 adjacent to the back waist edge 138. These laterally oriented attachment zones may have equal areas or may be unequal in area.

Alternatively, each attachment zone may extend laterally across the full width of the respective side flap. For example, a laterally oriented attachment zone may extend laterally from the chassis left side edge 137a to the left side flap edge 157a and thereby attach the entire width of the left side flap 147a adjacent to the front waist edge 136 to the interior surface 102 of the chassis 100. In embodiments in which the front edge 236 or the back edge 238 of the absorbent assembly 200 coincides with the respective front waist edge 136 or back waist edge 138 of the chassis 100 and the side flaps 147 overlap the absorbent assembly 200, the side flaps 147 may be attached to the absorbent assembly 200 instead of, or in addition to, being attached to the interior surface 102 of the chassis 100.

Between the attachment zones, the proximal edges 157 of the side flaps 147 remain free, i.e., are not attached to the interior surface 102 of the chassis 100 or to the absorbent assembly 200. Also between the attachment zones, each side flap preferably includes a longitudinally extensible flap elastic gathering member that is attached adjacent to the proximal edge of the side flap by any of many well-known means. Each such flap elastic gathering member may be attached over its entire length or over only a portion of its length. For example, such a flap elastic gathering member may be attached only at or near its longitudinally opposing ends and may be unattached at the middle of its length. Such a flap elastic gathering member may be disposed in the crotch region 37 and may extend into one or both of the front waist region 36 and the back waist region 38. For example, in the exemplary chassis 100 shown in FIG. 1, an elastic strand 167 is attached adjacent to the proximal edge 157 of each of the side flaps 147 and extends into both the front waist region 36 and the back waist region 38.

Each flap elastic gathering member may be enclosed inside a folded hem. For example, in the exemplary chassis 100 shown in FIG. 4 and FIG. 5, each of the elastic strands 167 is enclosed inside a hem 170 formed adjacent to the proximal edge 157 of the respective side flap 147. Alternatively, the flap elastic gathering member may be sandwiched between two layers of the chassis, e.g., between the layers of a laminate backsheet or between a backsheet and an inner liner. As another alternative, the flap elastic gathering member may be attached on a surface of the chassis 100 and remain exposed.

Figure 10:
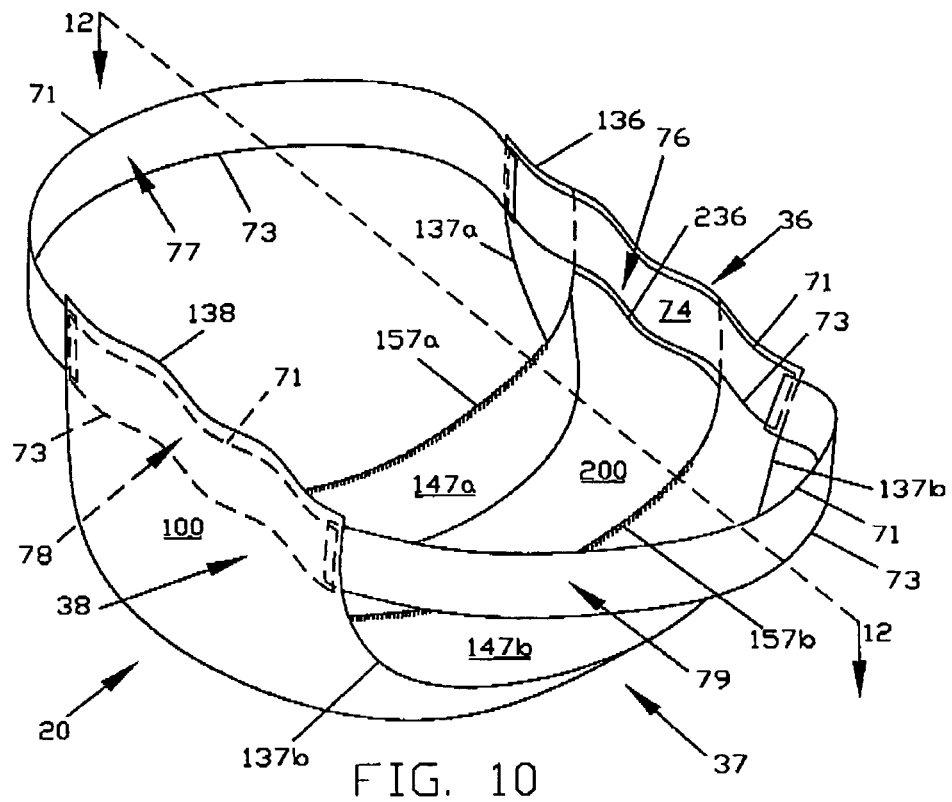
FIG. 10 is a perspective view of an exemplary diaper 20, which is shown with the interior portion of the diaper 20 facing upward.

When stretched, the flap elastic gathering member adjacent to each side flap edge allows the side flap edge to extend to the flat uncontracted length of the chassis, e.g., the length of the chassis 100, as shown in FIG. 1. When allowed to relax, the flap elastic gathering member contracts to gather the portion of the side flap edge along which the flap elastic gathering member is attached and thereby make the relaxed length of the side flap edge less than the flat uncontracted length of the chassis. For example, when the exemplary diaper 20 is in a relaxed condition as shown in FIG. 10, the elastic strands 167 contract to gather the proximal edges 157 of the side flaps 147. The contractive forces of the elastic strands 167 are transmitted at the respective front attachment zones 151 and at the respective back attachment zones 152 to the interior surface 102 of the chassis 100. These contractive forces pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because each of the proximal edges 157 remains free between the attachment zones 151 and 152, the contractive force of the elastic strand 167 lifts the proximal edge 157 away from the interior surface 102 of the chassis 100. As shown in FIG. 10, this lifting of the proximal edges 157 when the diaper 20 is in the relaxed condition lifts the side flaps 147 into position to serve as side barriers adjacent to the side edges 237 of the absorbent assembly 200.

When the diaper 20 is worn, the relaxed "U" shape generally conforms to the body of the wearer such that the front waist region 36 and the back waist region 38 are positioned such that they partially encircle the waist and the legs of the wearer. When the diaper 20 is worn in this manner, the elastic strands 167 tend to hold the lifted proximal edges 157 of the side flaps 147 in contact with the body of the wearer and thereby form seals to help prevent the leakage of deposited bodily waste out of the diaper 20. The lateral spacing of the lifted proximal edges 157 is selected to allow the deposit of bodily wastes from the lower torso of the wearer into the space between the lifted side flaps 147 and thereby directly onto the absorbent assembly 200. The width of each of the side flaps 147 in effect becomes its height when the free portion of its proximal edge is lifted and the side flap serves as a side barrier to leakage. This height is preferably selected to allow the lifted proximal edges 157 to fit into the leg creases of the body of the wearer at the same time as the absorbent assembly 200 is held in contact with the body.

Figure 2:
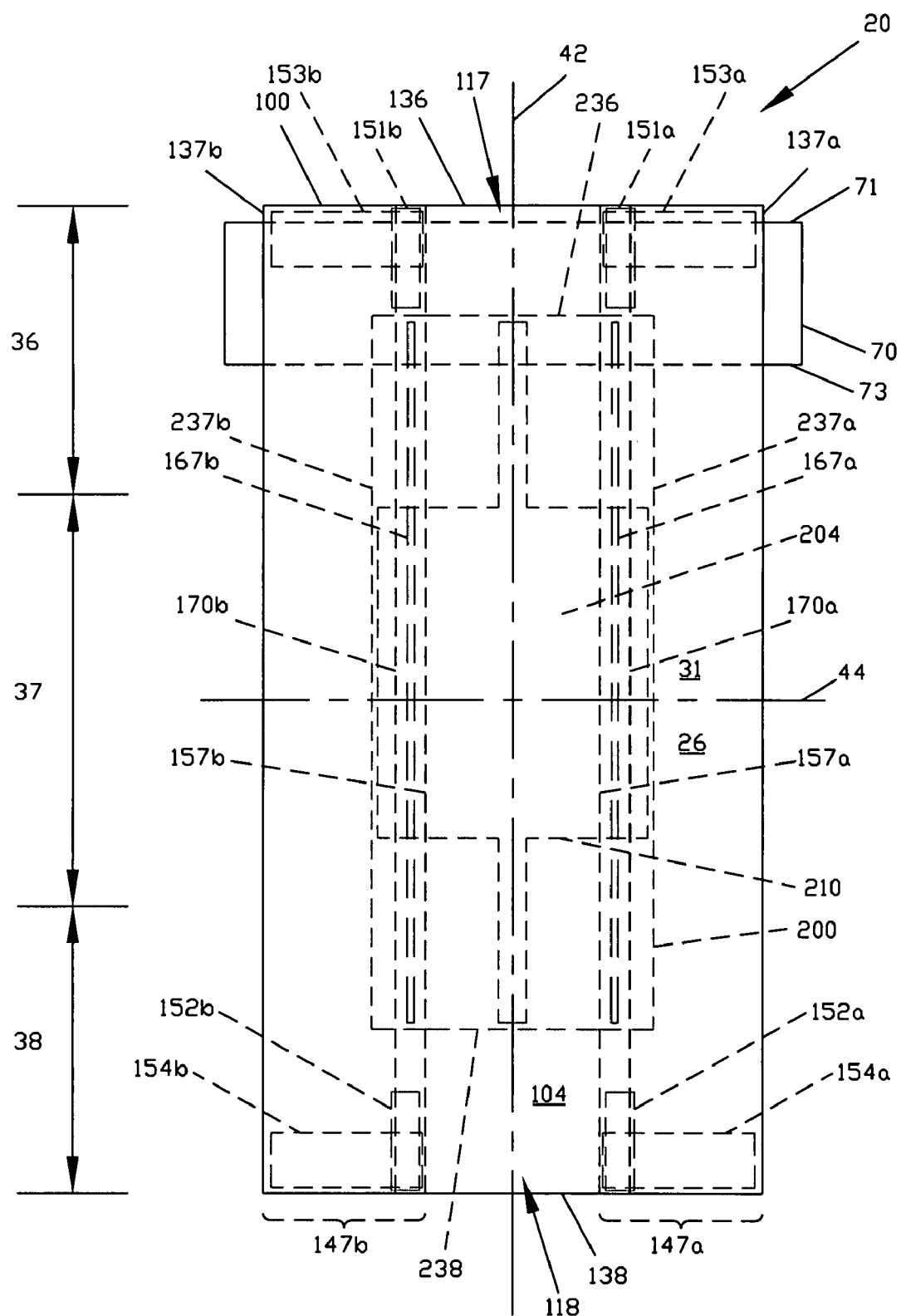
FIG. 2 is a plan view of the diaper 20 of FIG. 1 with the exterior portion of the diaper 20 shown facing the viewer.

In the finished diaper, the chassis may have a generally rectangular shape, as in the exemplary diaper 20 shown in FIG. 1 and FIG. 2. Such a generally rectangular configuration may be desirable in order to minimize the amount of waste material and the difficulty associated with the manufacture of the diaper 20.

A portion or the whole of the chassis 100 may be made extensible to a degree greater than the inherent extensibility of the material or materials from which the chassis is made, e.g., the backsheet 26, the inner liner 22, or both. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to provide additional body coverage for wearers of differing size, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to adequately cover a wearer that is larger than the unextended smaller diaper would fit. In other words, a lesser amount of material is needed in order to make a diaper capable of providing adequate coverage for a given size of a wearer when the material is made extensible as described. The portion of the chassis in one of the waist regions may be made laterally extensible to a maximum extensibility greater than a maximum extensibility of another portion of the chassis in the crotch region such that a lateral extension of each of the portions to its maximum extensibility imparts an hourglass shape to the chassis.

Figure 11:
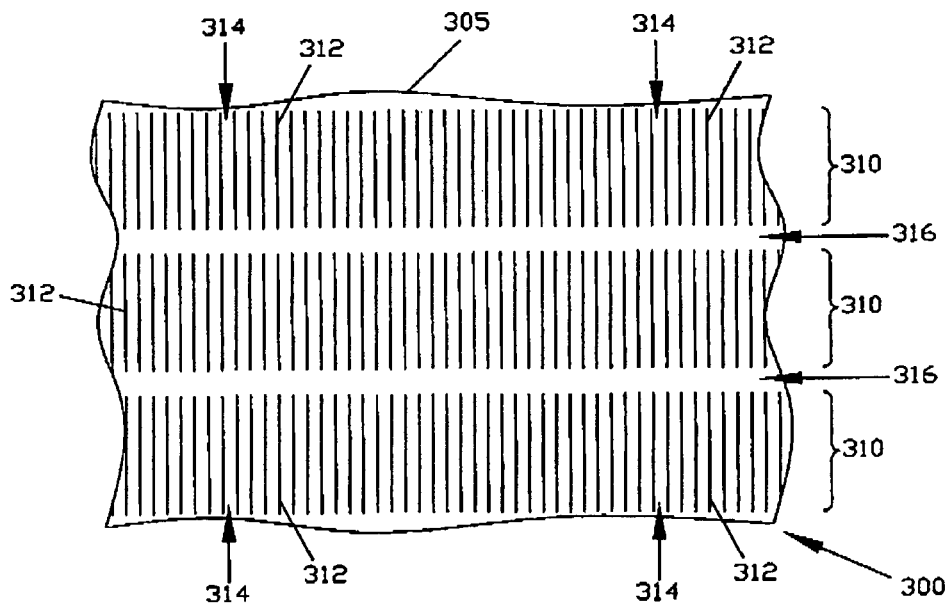
FIG. 11 is a plan view of an exemplary fragment of a formed web material.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 11. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

The front laterally central portion 117 and the back laterally central portion 118 of the chassis 100 between the attachment zones 151, 152, 153, and 154 where the side flaps 147a and 147b are attached to the interior surface 102 of the chassis adjacent to the respective waist edges 137 and 138 may have a different range of extensibility from the portions of the chassis in the attachment zones. Additionally or alternatively, the laterally central portions 117 and 118 may be extensible to a greater or lesser degree when subjected to a given level of opposing tensile forces, i.e., may be more easily or less easily extensible, than the portions of the chassis in the attachment zones. For example, if the chassis is made uniformly extensible across its entire width prior to the formation of the side flaps, the double layering in the areas of the attachment zones after the formation of the side flaps may have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis may be deformed to a greater or a lesser degree than the altered regions in the attachment zones to render the laterally central portions more easily or less easily extensible than the respective portions in the attachment zones.

Description of the Support Element

The support element 70 encircles the waist of the wearer so as to support the waist regions 36 and 38 of the diaper 20 adjacent to the waist of the wearer and thereby position the absorbent assembly 200 appropriately to receive and contain urinary and fecal waste excreted by the wearer. The support element has the form of a belt, i.e., a waist-encircling element suitable for holding the disposable absorbent article 20 against the body of the wearer.

As shown in FIG. 3, FIG. 7, FIG. 8, FIG. 9, FIG. 10, FIG. 12, FIG. 13, FIG. 14, FIG. 15, FIG. 16, and FIG. 17, the support element 70 is made up of four panels arranged circumferentially to form a continuous loop. The front panel 76 of the support element 70 is attached to the interior surface 102 of the chassis 100 in the front waist region 36 of the diaper 20 and extends circumferentially across a portion or all of the lateral extent of the chassis 100 in that waist region. The back panel 78 is attached to the interior surface 102 of the chassis 100 in the back waist region 38 of the diaper 20 and extends circumferentially across a portion or all of the lateral extent of the chassis 100 in that waist region. The left hip panel 77 is attached to the front panel 76 and to the back panel 78 and extends circumferentially between them over the left hip of the wearer. The right hip panel 79 is likewise attached to the front panel 76 and to the back panel 78 and extends circumferentially between them over the right hip of the wearer.

The interior surface 74 of the front panel 76 and the interior surface 86 of the back panel 78 contact the skin of the wearer when the diaper 20 is worn. As shown in the figures, each of the right hip panel 79 and the left hip panel 77 likewise contacts the skin of the wearer when the diaper 20 is worn. Thus, the interior surface 74 of the front panel 76 and the interior surface 86 of the back panel 78 in combination with the left hip panel 77 and the right hip panel 79 contact the skin around the waist of the wearer. Each of the front panel 76 and the back panel 78, as well as each of the hip panels 77, 79 is preferably formed of a soft material that will not irritate the skin of the wearer. Marty suitable materials are known in the art, including rayon and synthetic nonwovens such as spunbonded or carded polypropylene or polyester or other olefinic materials.

Figure 15:
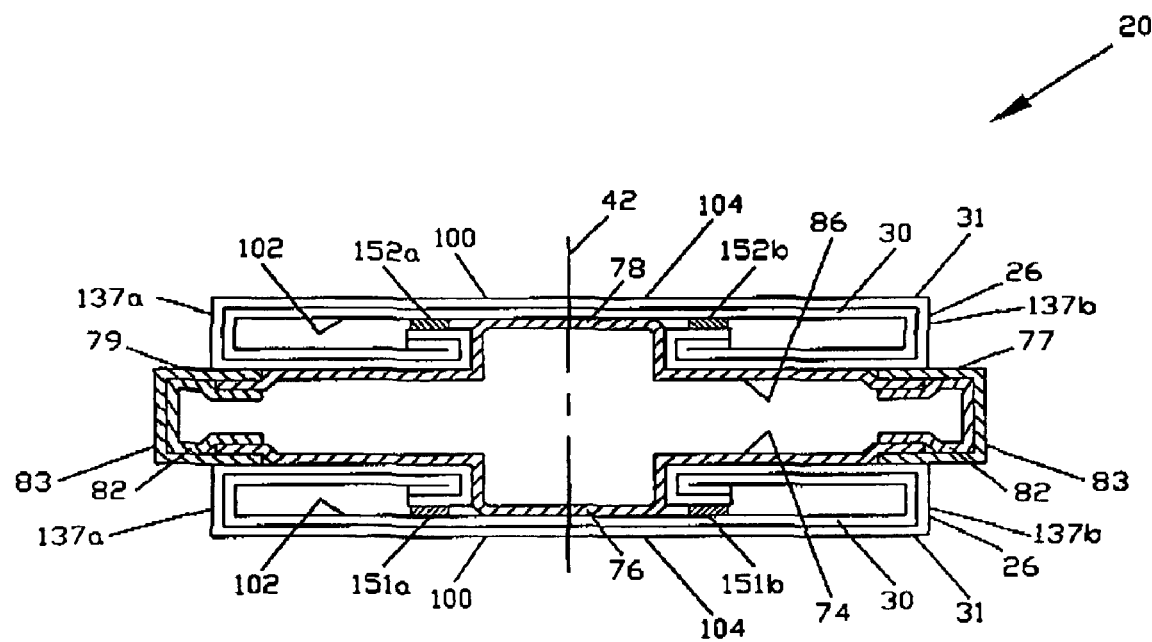
FIG. 15 is a view of an exemplary diaper taken at the section line 12-12 of FIG. 10.
Figure 16:
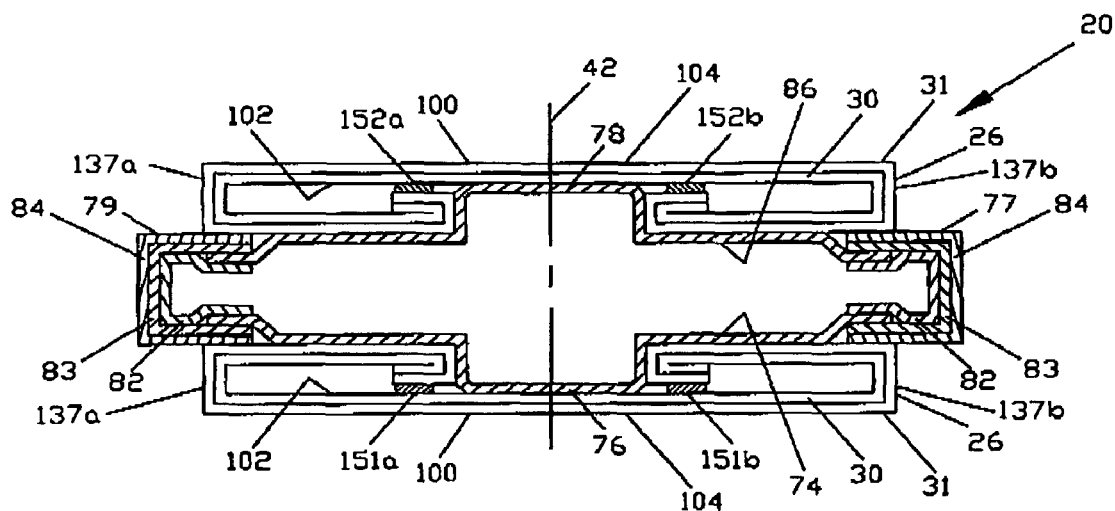
FIG. 16 is a view of an exemplary diaper taken at the section line 12-12 of FIG. 10.

As shown in FIG. 15 and FIG. 16, each hip panel may have a laminate structure. For example, each hip panel may include a skin-contacting layer 82 and an additional layer or layers disposed exteriorly of the skin-contacting layer. An elastic version of one of the aforementioned suitable materials, such as a nonwoven exhibiting substantial elastic properties, may be used for the skin-contacting layer 82. Each hip panel may include a skin-contacting layer 82 and an elastic layer 83 laminated to the skin-contacting layer 82, as shown in FIG. 15 and FIG. 16. When stretched in the circumferential direction, the elastic layer 83 resists by providing a contractive force tending to draw the front panel 76 and the back panel 78 toward each other circumferentially. Suitable materials for the elastic layer 83 are well-known in the art, including natural rubber strands, synthetic rubber strands, elastomeric films, etc. The material chosen for the elastic layer 83 preferably exhibits a force response proportional to its elongation. Each hip panel may also include an exterior cover layer 84 laminated to the elastic layer 83 on its surface opposite the skin-contacting layer 82, thereby forming a trilaminate in which the elastic layer 83 is sandwiched between the skin-contacting layer 82 and the exterior cover layer 84, as shown in FIG. 16.

The layers of each hip panel may be laminated by any method suitable for the elements being attached together and their constituent materials. For example, the elastic layer 83 may be maintained in a stretched condition while being attached to a relaxed skin-contacting layer 82 (and a relaxed exterior cover layer 84 if present) and then allowed to relax. The resultant contraction of the elastic layer 83 may gather the skin-contacting layer 82 in such a way as to create rugosities and the laminate thus formed may be extended in the direction of the original stretch up to the original dimension of the skin-contacting layer 82 (and the exterior cover layer 84 if present) with only the elastic layer 83 resisting the extension. A similar result may be achieved by, for example, first gathering the skin-contacting layer 82 (and the exterior cover layer 84 if present), such as by pleating it, and then attaching the elastic layer 83 in a relaxed condition. The resultant laminate may be extended in a direction perpendicular to the pleat ridges up to the original dimension of the skin-contacting layer 82 (and the exterior cover layer 84 if present) with only the elastic layer 83 resisting the extension.

Figure 17:
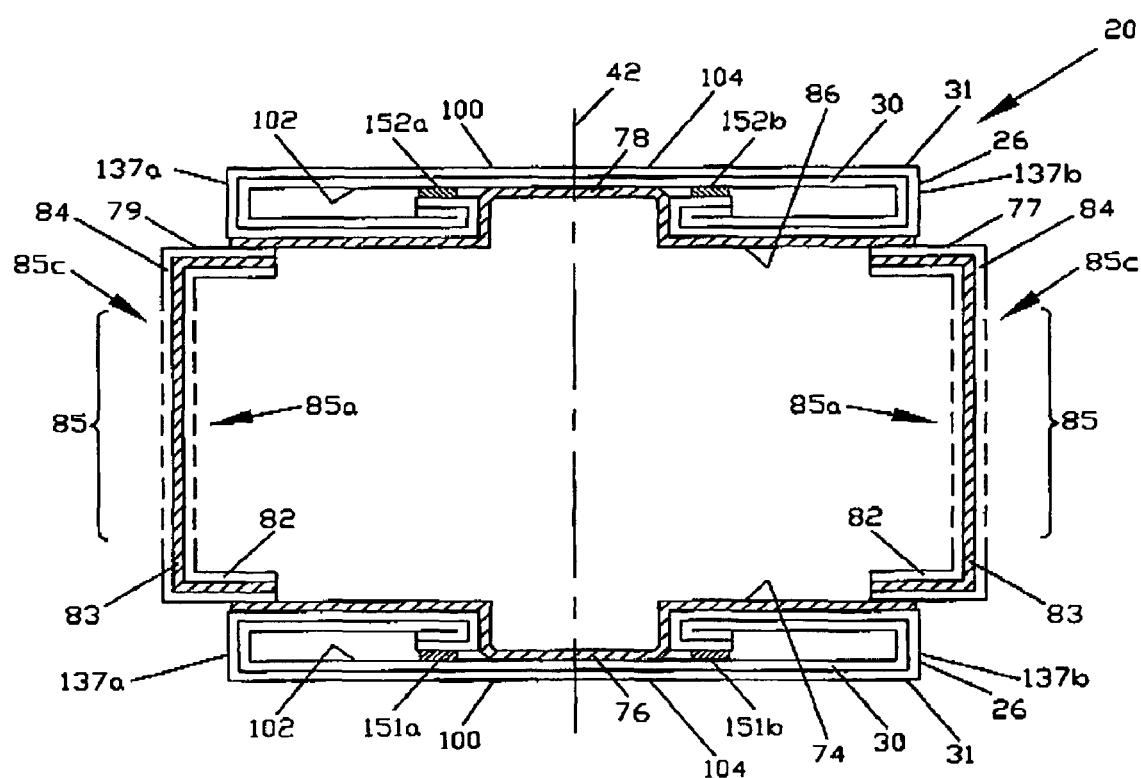
FIG. 17 is a view of an exemplary diaper taken at the section line 12-12 of FIG. 10.

In some exemplary methods, the lamination may be performed with both the elastic layer 83 and the skin-contacting layer 82 (and the exterior cover layer 84 if present) relaxed. All or a portion of the resultant laminate hip panel may subsequently be "activated" by subjecting it to elongation to create localized ruptures in a portion 85a of the skin-contacting layer 82 (and a portion 85c of the exterior cover layer 84 if present). In FIG. 17, a stretched left hip panel 77 and a stretched right hip panel 79 each having an activated portion 85 are shown, with the ruptured portion 85a of the skin-contacting layer 82 and the ruptured portion 85c of the exterior cover layer 84 shown in dashed lines representing exemplary breaks in and/or separation of the fibers in nonwoven materials. The ruptured portion 85a of the skin-contacting layer 82 (and the ruptured portion 85c of the exterior cover layer 84 if present) in the resultant activated portion 85 of the laminate provides little or no resistance to extension in the direction of the original elongation. For example, when a nonwoven is used for the skin-contacting layer 82 (and the exterior cover layer 84 if present), the ruptured portion(s) typically include(s) breaks in and/or separation of the fibers that render the ruptured portion(s) substantially incapable of transmitting tensile forces in the plane of the nonwoven. Some suitable activation methods are known in the art as "ring-rolling" processes. In such processes, it is typically desirable to attach the ruptured portion 85a of the skin-contacting layer 82 (and the ruptured portion 85c of the exterior cover layer 84 if present), to the elastic layer 83 in a sufficiently dense area coverage as to ensure that the appearance of the activated portion of the laminate is not substantially degraded by the presence of loose tufts of fibers as a result of the rupture caused during the activation process.

A combination of lamination methods may be used, if desired, so long as they are suitable for the elements being attached together and their constituent materials.

Figure 3:
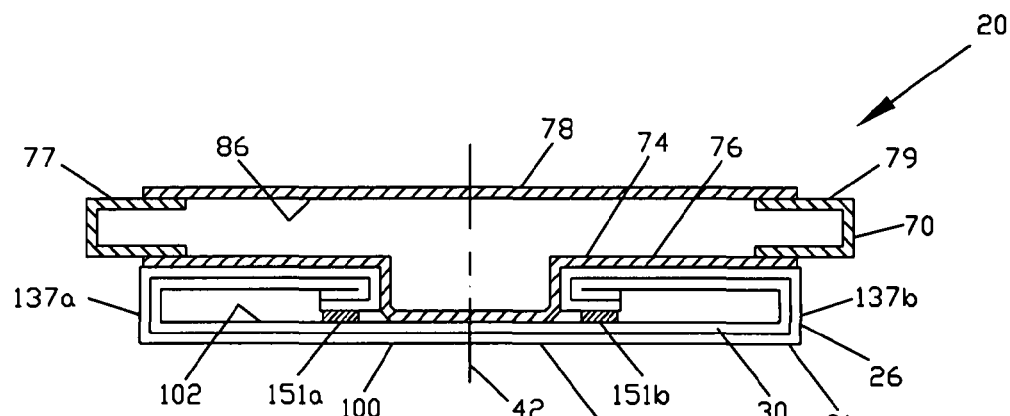
FIG. 3 is a section view of the diaper 20 of FIG. 1 taken at the section line 3-3.
Figure 4:
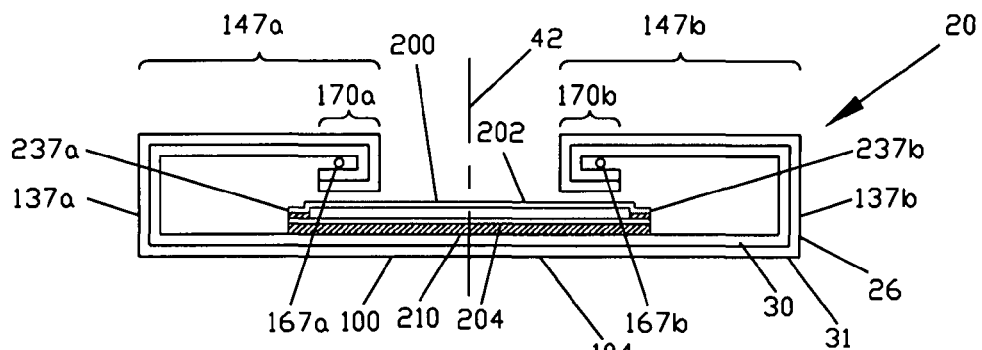
FIG. 4 is a section view of the diaper 20 of FIG. 1 taken at the section line 4-4.
Figure 5:
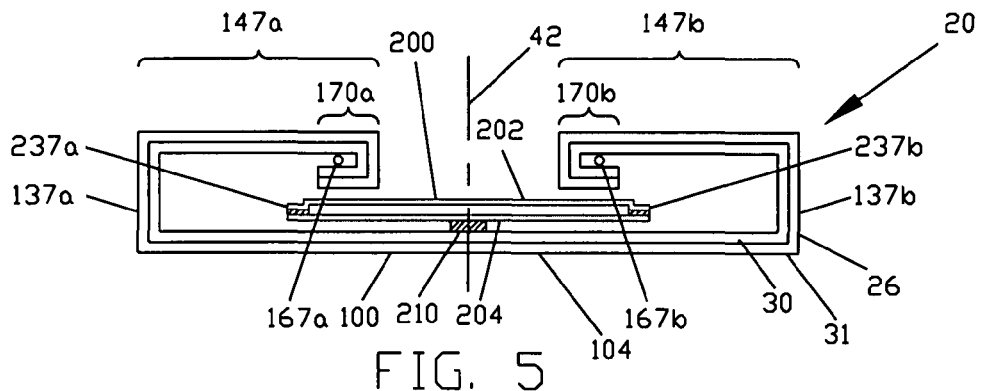
FIG. 5 is a section view of the diaper 20 of FIG. 1 taken at the section line 5-5.
Figure 6:
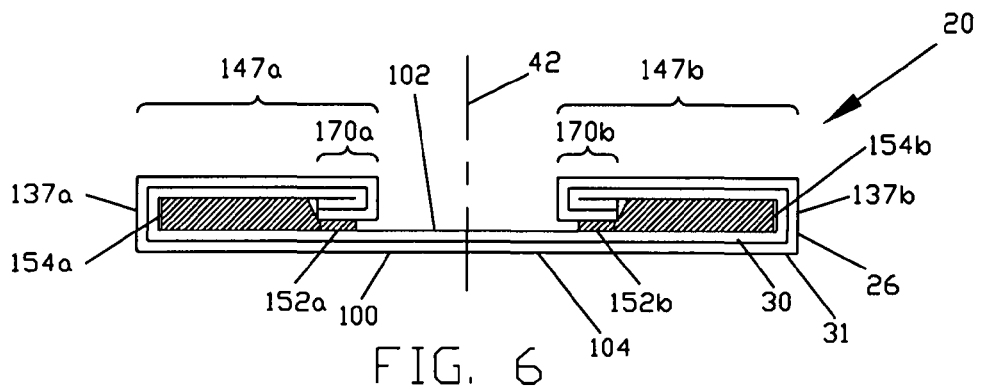
FIG. 6 is a section view of the diaper 20 of FIG. 1 taken at the section line 6-6.
Figure 12:
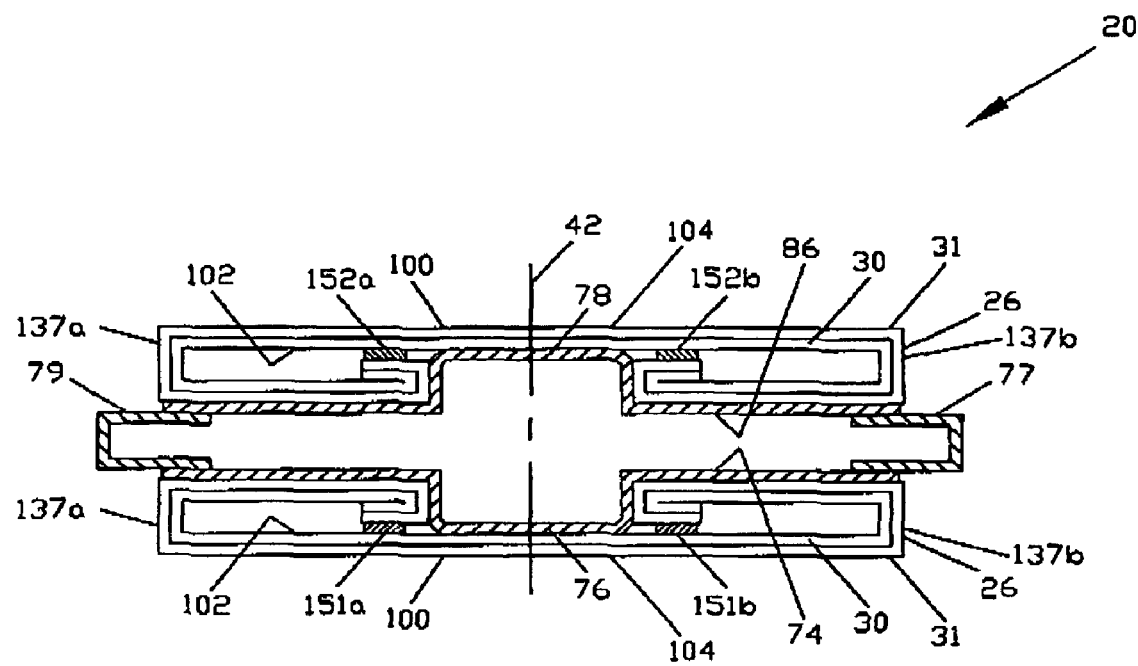
FIG. 12 is a view of an exemplary diaper taken at the section line 12-12 of FIG. 10.
Figure 13:
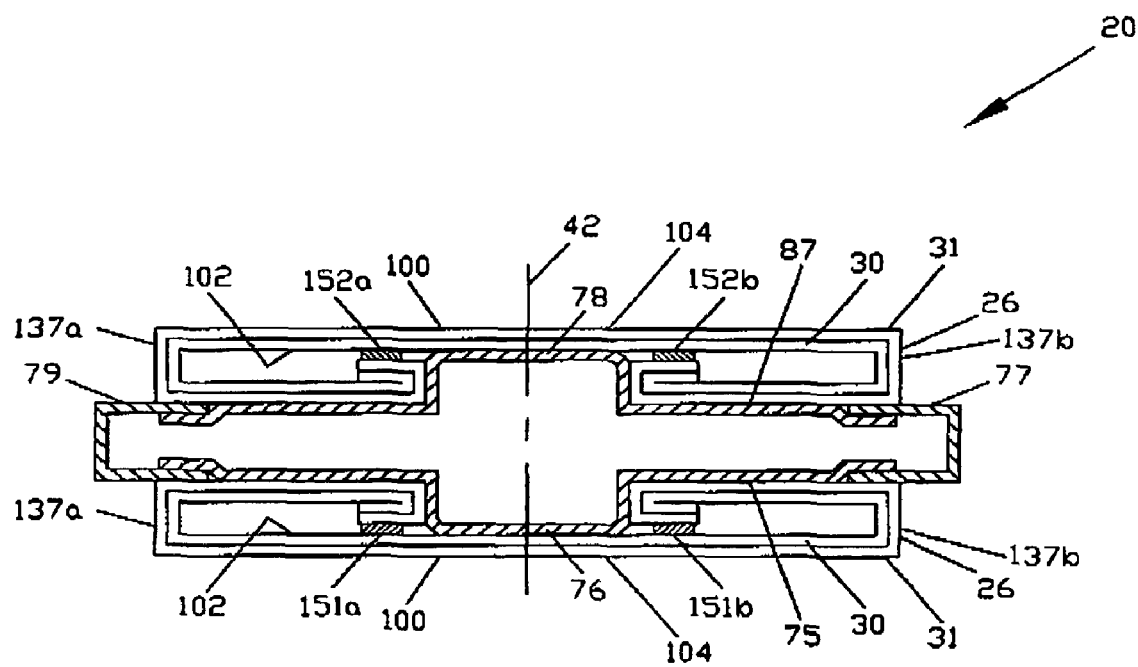
FIG. 13 is a view of an exemplary diaper taken at the section line 12-12 of FIG. 10.
Figure 14:
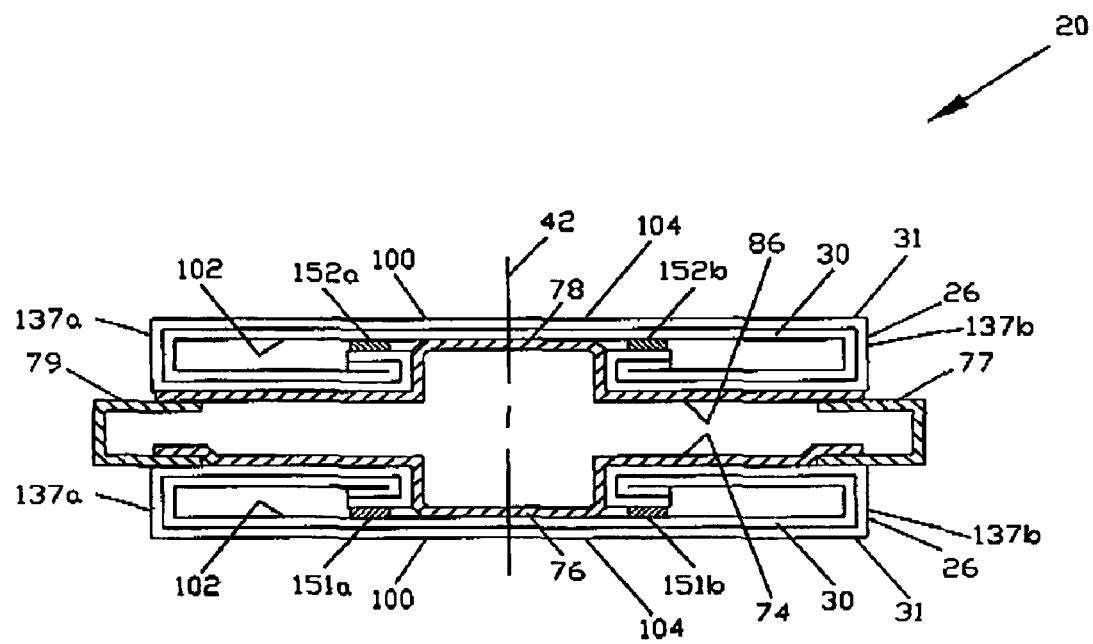
FIG. 14 is a view of an exemplary diaper taken at the section line 12-12 of FIG. 10.

In some embodiments, the hip panels 77, 79 may be attached to the interior surface 74 of the front panel 76 and the interior surface 86 of the back panel 78, for example as shown in FIG. 3, FIG. 10, and FIG. 12. In some embodiments, the hip panels 77, 79 may be attached to the exterior surface 75 of the front panel 76 and the exterior surface 87 of the back panel 78, for example as shown in FIG. 13. In some embodiments, the hip panels 77, 79 may be attached to the interior surface of either of the front panel 76 and the back panel 78 and to the exterior surface of the other, for example as shown in FIG. 14. In some embodiments, the front panel 76 and/or the back panel 78 may be sandwiched between layers of the left hip panel 77 and/or the right hip panel 79, for example as shown in FIG. 15 and FIG. 16.

Figure 18:
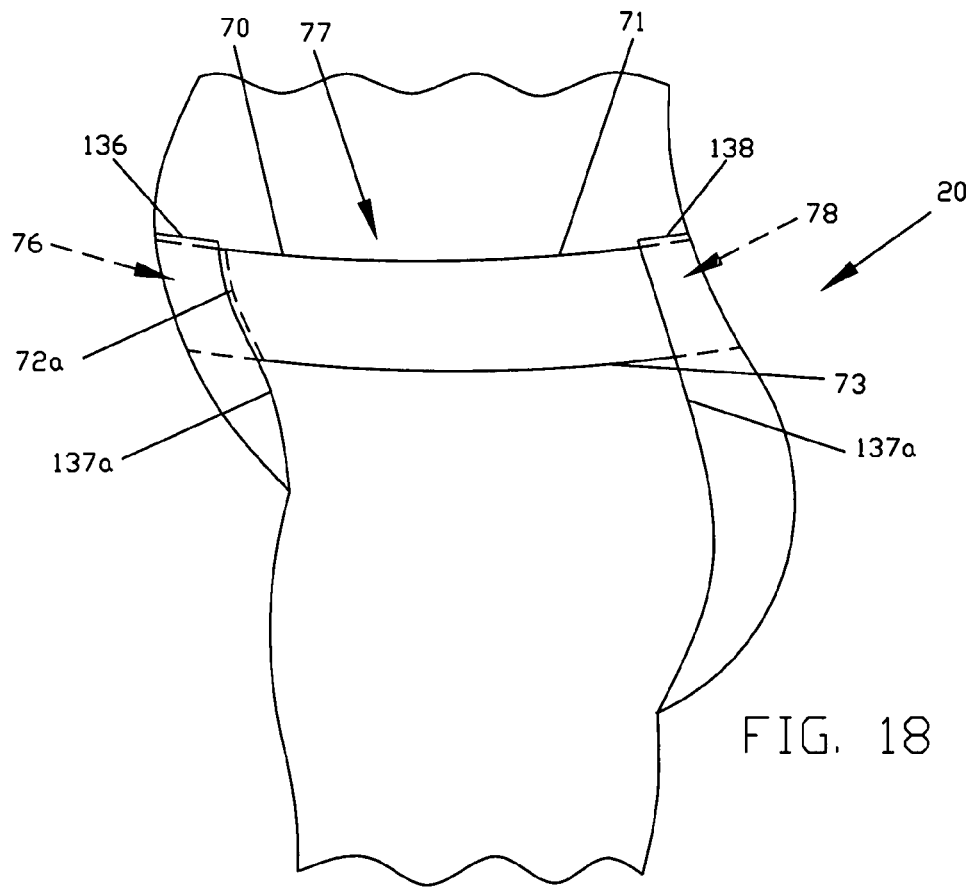
FIG. 18 is a simplified side elevation view of an exemplary diaper 20 being worn about a lower torso of a wearer.
Figure 19:
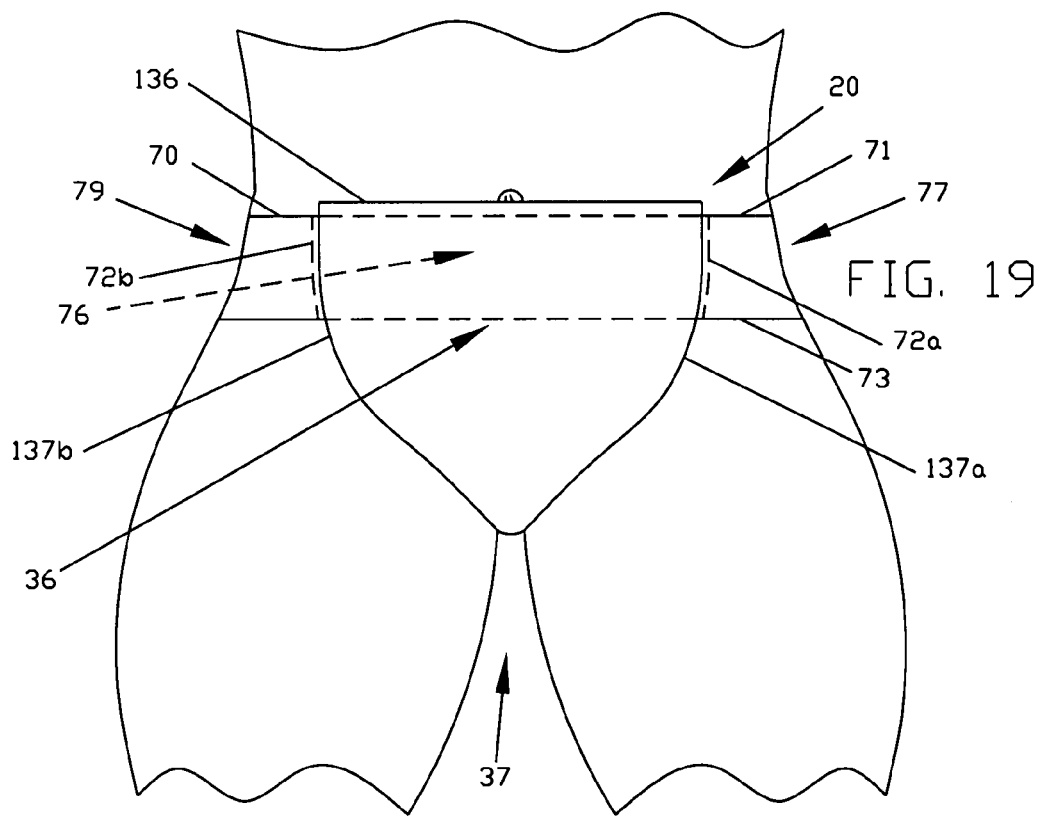
FIG. 19 is a front elevation view of the diaper 20 of FIG. 18.

Some users may desire to tear open the diaper 20 in order to remove it from the body of the wearer. In order to provide guidance to such a user regarding where the product may be torn open, a visible tear locator line may be printed on the support element 70. For example, a pair of laterally opposing tear locator lines 72a, 72b may be printed exteriorly on the hip panels 77, 79 adjacent to the front panel 76 as shown in FIG. 18 and FIG. 19. In embodiments in which laminate hip panels containing a nonwoven are activated as described herein, the laminate structure may be torn relatively easily in the ruptured portion 85 in a direction generally perpendicular to the direction in which the laminate was elongated during the activation process, because the breaks in and/or separation of the fibers in the nonwoven cause a zippering effect. Once a tear in this direction is started by the application of a tensile force in the direction of this elongation, the tear can be propagated relatively easily. Thus, for example, a user can initiate a tear by applying a generally laterally oriented tensile force across the tear locator line 72 at or adjacent to the laterally extending distal edge 71 then relatively easily propagate that tear all the way to the proximal edge 73 by continuing to apply a tensile force in the same direction. Tearing the hip panels 77, 79 at both of the laterally opposing tear locator lines 72 will release the diaper 20 from the waist and both legs of the wearer. Such tear locator lines 72 may be printed on the hip panels 77, 79 adjacent to the back panel 78 instead of, or in addition to, adjacent to the front panel 76. For some users, locating the tear locator lines 72 adjacent to the front panel 76 may be preferable, because they may prefer to lay their infants down on their backs while removing the diapers, for example. In such usage, tear locator lines 72 disposed adjacent to the front panel 76 are likely to be more easily visible than tear locator lines 72 disposed adjacent to the back panel 78.

Figure 20:
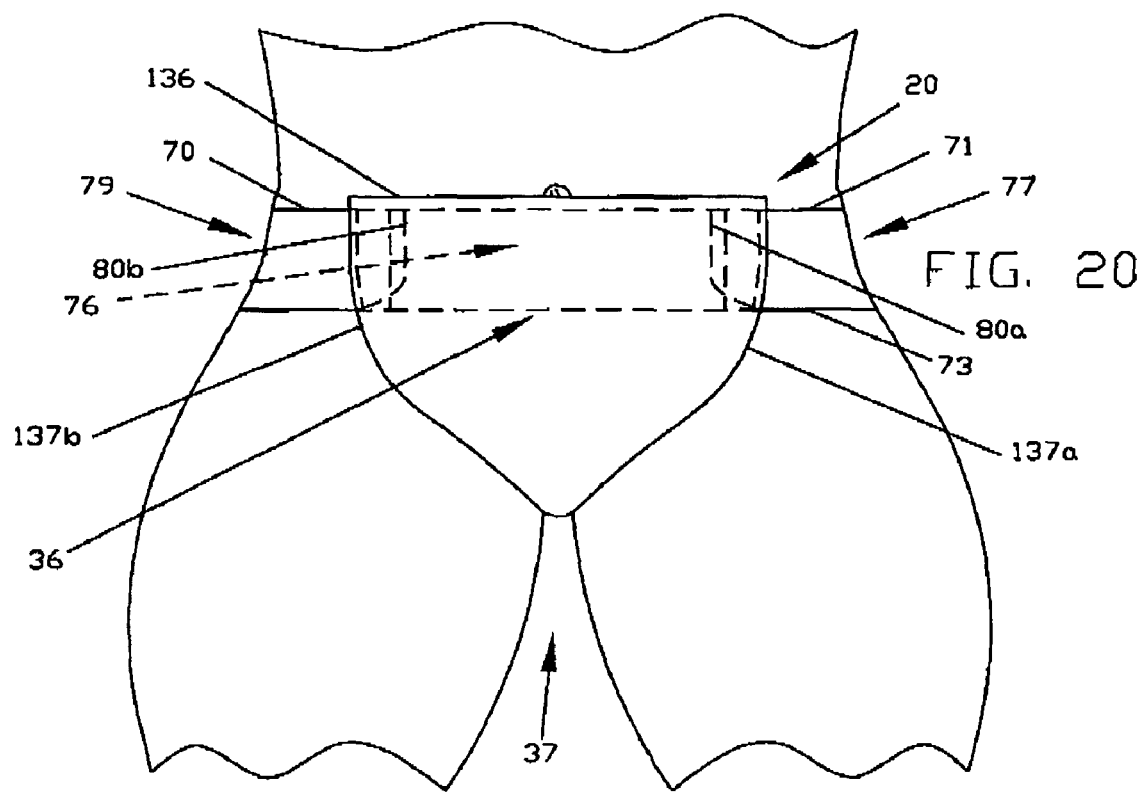
FIG. 20 is a front elevation view of another exemplary diaper 20.
Figure 21:
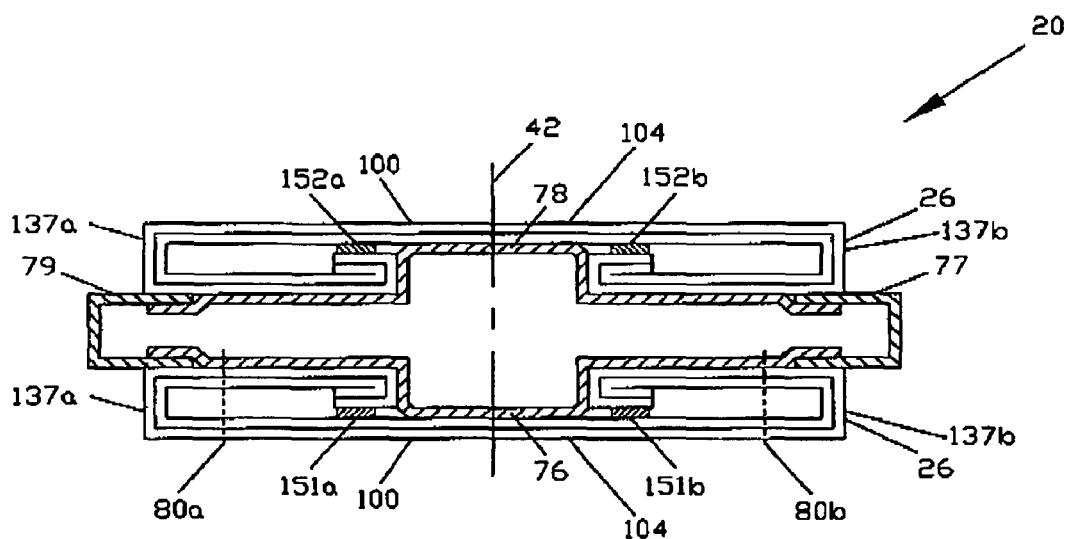
FIG. 21 is a view of an exemplary diaper taken at a section line similar to section line 12-12 of FIG. 10.

In order to minimize the level of tensile force required to tear open the diaper 20 for removal from the wearer, frangible tear lines may be provided. Such a frangible tear line may be formed in a layer or a laminate of layers by perforation, by the formation of a brittle area or areas at which the material will preferentially fracture when stressed, by the formation of a weaker area or areas at which the material will preferentially tear when stressed, by the formation of a friable area or areas at which the material will preferentially crumble when stressed and/or bent, or by any other method of providing frangibility that is suitable for the materials involved. For example, a pair of laterally opposing frangible tear lines 80a, 80b may be formed in the hip panels 77, 79 and the front panel 76, as well as the portion of the chassis 100 overlain by the front panel, as shown in FIG. 20 and FIG. 21. In this embodiment, the frangible tear lines 80 intersect the distal edge 71 of the support element 70 laterally inboard of the hip panels 77, 79 and intersect the proximal edge 73 of the support element 70 at the intersection of the proximal edge 73 and the side edge 137 of the chassis 100 at the margin of each leg opening. The frangible tear lines 80 may be disposed elsewhere, but the depicted configuration may be preferred in some embodiments. For example, it has been found that when a nonwoven is used in an activated laminate hip panel structure, perforation of this structure in the activated portion may result in unintentionally tearing open the diaper along the perforation, apparently because the perforation further weakens the already weakened ruptured portion. This premature tearing starts predominately at the proximal edge 73. It has been found that disposing the frangible tear lines 80 such that they intersect the distal edge 71 of the support element 70 laterally inboard of the hip panels 77, 79 significantly reduces the likelihood of occurrence of such premature tearing along the perforation. Of course, if the frangible tear lines 80 continued generally linearly toward the lateral axis 44, continuous portions of the diaper 20 would remain in place around the legs of the wearer. Therefore, the frangible tear lines 80 are shaped to intersect the margins of the respective leg openings as described above. With this configuration, tearing the diaper 20 at both of the laterally opposing frangible tear lines 80 will release the diaper 20 from the waist and both legs of the wearer. Such frangible tear lines 80 may be disposed in the back panel 78 instead of, or in addition to, the front panel 76. For some users, locating the frangible tear lines 80 in the front panel 76 may be preferable, because they may prefer to lay their infants down on their backs while removing the diapers, for example. In such usage, frangible tear lines 80 in the front panel 76 are likely to be more easily visible and more easily usable than frangible tear lines 80 disposed in the back panel 78.

In some embodiments, both frangible tear lines 80 and tear locator lines 72 may be provided. For example, tear locator lines 72 may be printed at or adjacent to frangible tear lines 80. In such an embodiment, the presence of the visible tear locator lines 72 may prove helpful to the user in locating the frangible tear lines 80 for use in removal of the diaper 20.

The support element 70 having the four-piece structure described herein is easier to process than the forms of stretch waistbands and stretch side panels typically used in diapers in the past. For example, the entire support element 70 can be formed separately and then introduced into a continuous production process as a discrete element that can be attached onto the front waist region 36 or the back waist region 38 of a diaper 20 in-process. Unlike typical waistbands and/or side panels that bridge from one diaper to the next in the process and must be cut through when successive diapers are severed from each other to form individual finished products, the support element 70 is simply attached to the chassis 100 in a first of the waist regions within the boundary of each particular diaper 20 and need not be cut when that diaper 20 is severed from the continuous webs of materials.

Also, unlike typical stretch side panels, the pre-formed support element 70 has no laterally protruding flap or ear having a free end that must be controlled in the process in such a way as to avoid damage during its movement through the process equipment. Instead, once the support element 70 that has been pre-formed into a continuous loop has been attached to the chassis 100 in a first of the waist regions, it can be controlled relatively easily until the point in the process at which it is attached to the second waist region. Additionally, because a diaper is typically folded toward its interior in preparation for packaging, the support element 70 that is attached to the interior surface 102 of the chassis 100 is ideally located for attachment to the second waist region in conjunction with this step of folding the diaper 20.

This structure is also desirable from the standpoints of comfort and appearance. For example, unlike typical stretch side panels, the support element 70 has no seam over the hip of the wearer. Instead, each hip panel smoothly overlies the hip with no potentially uncomfortable or unsightly discontinuity in its entire circumferential span between where it is attached to the front panel 76 and where it is attached to the back panel 78.

Description of the Absorbent Assembly

Figure 24:
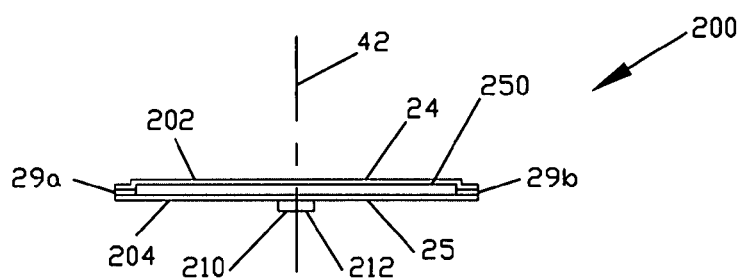
FIG. 24 is a view of the absorbent assembly of FIG. 22 taken at the section line 24-24.
Figure 25:
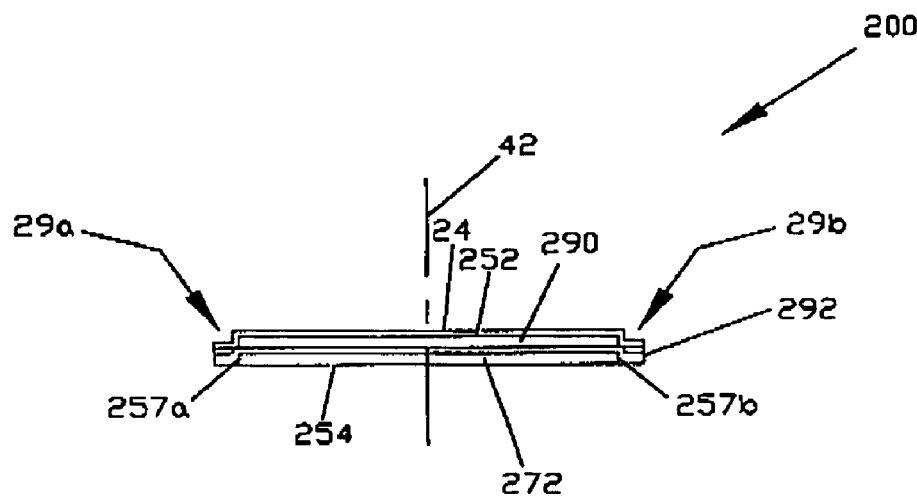
FIG. 25 is a section view of an exemplary absorbent assembly 200.
Figure 26:
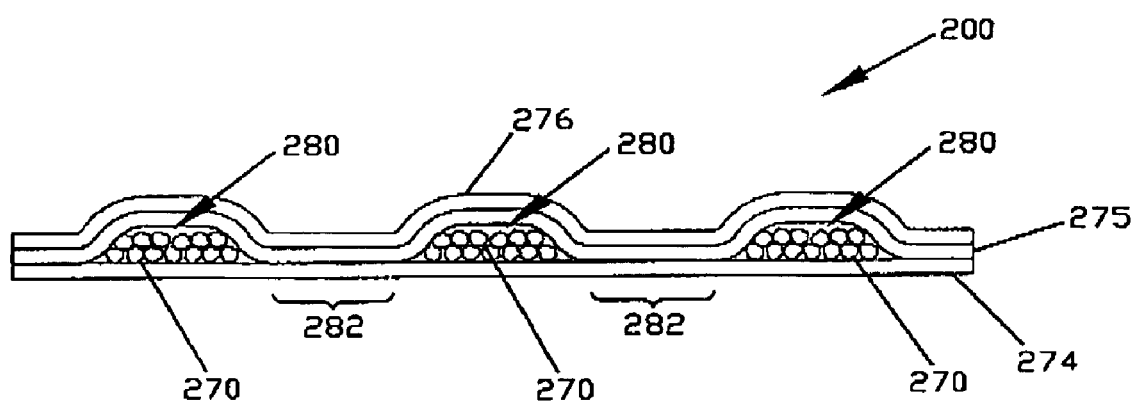
FIG. 26 is a section view of an exemplary absorbent assembly 200.

As shown in FIG. 24, FIG. 25, and FIG. 26 the absorbent assembly 200 includes an absorbent core 250 that serves to absorb and retain liquid bodily waste materials. The absorbent core 250 has a laterally extending front edge 256 and a longitudinally opposing and laterally extending back edge 258. The absorbent core 250 also has a longitudinally extending left side edge 257a and a laterally opposing and longitudinally extending right side edge 257b, both absorbent core side edges extending longitudinally between the front edge 256 and the back edge 258. The absorbent core 250 also has an interior surface 252 and an exterior surface 254.

The absorbent assembly 200 may be attached to the interior surface 102 of the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern.

An exemplary contiguous cruciform attachment pattern 210 is shown in FIG. 2, FIG. 4, FIG. 5, FIG. 22, FIG. 23, and FIG. 24. The portions of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in these figures leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in these figures prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness and positioning of the side flaps 147 when the elastic strands 167 lift the proximal edges 157 into contact with the body of the wearer. For example, if the absorbent assembly was attached only along the longitudinal centerline, the absorbent assembly could be compressed by the legs to a smaller lateral dimension than desired. This narrowing of the absorbent assembly would in turn allow the chassis 100 in the crotch region 37 to narrow, i.e., allow the side edges 137 to move toward the longitudinal axis 42. Such narrowing of the chassis 100 would increase the likelihood that the side flaps 147 would distort and fail to maintain contact with the body and/or become improperly positioned. However, because the relatively wide laterally extending portion 214 of the cruciform attachment pattern 210 restrains the chassis 100 over a relatively wide portion of the width of the crotch region 37, the side flaps 147 are more likely to remain properly positioned while being lifted by the elastic strands 167.

Within the extent of the cruciform attachment pattern 210, the absorbent assembly 200 may be attached to the chassis 100 continuously or intermittently. For example, a film of an adhesive material may be applied continuously over the entire area of the cruciform attachment pattern and then used to continuously attach the absorbent assembly to the chassis. As an alternative example, an adhesive material may be applied discontinuously at and inside the boundaries of the cruciform attachment pattern, such as in the form of dots, stripes, beads, spirals, etc., and then used to attach the absorbent assembly to the chassis.

The cruciform attachment pattern 210 may be disposed symmetrically with respect to either or both of the longitudinal axis 42 and the lateral axis 44 of the chassis 100. Alternatively, the cruciform attachment pattern 210 may be disposed asymmetrically with respect to either or both of the longitudinal axis 42 and the lateral axis 44. In addition, the cruciform attachment pattern 210 may be disposed symmetrically with respect to either or both of the side edges 237 and the front edge 236 and the back edge 238 of the absorbent assembly 200. Alternatively, the cruciform attachment pattern 210 may be disposed asymmetrically with respect to either or both of the side edges 237 and front edge 236 and back edge 238.

Suitable configurations of cruciform attachment patterns are disclosed in U.S. Pat. No. 6,962,578 issued on 8 Nov. 2005.

The absorbent core 250 may be disposed between a lower covering sheet that is disposed on the exterior face of the absorbent core 250 and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in FIG. 22, FIG. 23, and FIG. 24, an upper covering sheet 24 and a lower covering sheet 25 are attached together at or adjacent to the side edges 237 of the absorbent assembly 200 in longitudinally extending attachment zones 29. Alternatively, the upper covering sheet 24 and the lower covering sheet 25 may be attached together in places other than the side edges 237, e.g., at or adjacent to the end edges 236 and 238 of the absorbent assembly 200, or at or adjacent to both the end edges 236 and 238 and the side edges 237. Both the upper covering sheet and the lower covering sheet are water vapor-permeable, i.e., breathable.

The upper covering sheet 24 is water-permeable and allows liquid waste to pass through to the absorbent core 250, where the liquid waste is absorbed. The lower covering sheet 25 may be water-impermeable. However, the lower covering sheet 25 is preferably water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 may form the interior surface 202 of the absorbent assembly 200 that is intended to be placed against the body of the wearer. The upper covering sheet 24 is preferably formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

Figure 22:
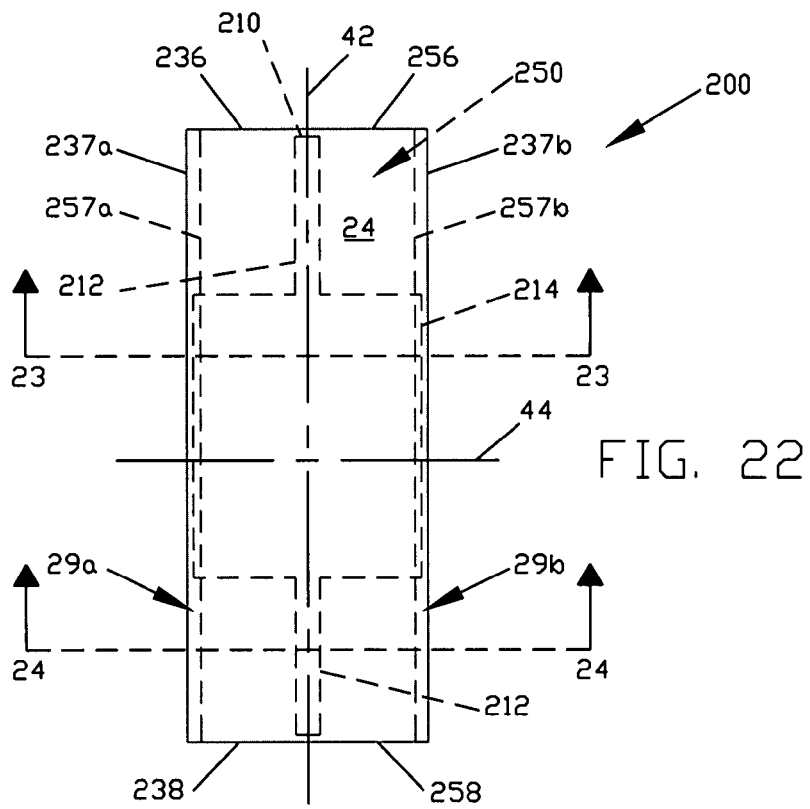
FIG. 22 is a plan view of an exemplary absorbent assembly 200 with the interior portion of the absorbent assembly 200 shown facing the viewer.
Figure 23:
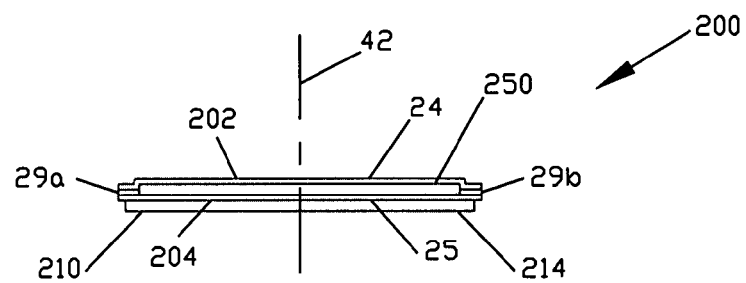
FIG. 23 is a view of the absorbent assembly of FIG. 22 taken at the section line 23-23.

In the exemplary absorbent assembly 200 shown in FIG. 22, FIG. 23, and FIG. 24, the upper covering sheet 24 and the lower covering sheet 25 are of the same size, i.e., both the upper covering sheet 24 and the lower covering sheet 25 extend to the front edge 236 and back edge 238, as well as to the side edges 237 of the absorbent assembly 200. Alternatively, the upper covering sheet 24 and the lower covering sheet 25 may differ in size. For example, the upper covering sheet may extend longitudinally only to an extent sufficient to cover the absorbent core and the lower covering sheet may extend longitudinally beyond the upper covering sheet toward or to the adjacent waist edge. Such an extended covering sheet may serve to isolate the skin of the wearer from a portion of the backsheet 26 as may be desirable, for example, when the diaper 20 is worn under conditions in which contact between the skin and a backsheet film could be uncomfortable.

As another example, the lower covering sheet 25 may be larger than the upper covering sheet 24 and may be wrapped over the side edges 257 of the absorbent core 250 onto the interior surface of the absorbent core 250, where the upper covering sheet 24 and the lower covering sheet 25 may be attached together. Alternatively, in place of a separate upper covering sheet 24 and a separate lower covering sheet 25, a single covering sheet may be wrapped around the absorbent core 250 and attached to itself to contain the absorbent core 250. Such a single covering sheet forms an upper layer and a lower layer when wrapped around the absorbent core 250 and, in general, the description of the separate upper covering sheet 24 and lower covering sheet 25 are intended to apply to such upper and lower layers of a wrapped single covering sheet.

The absorbent core 250 includes a storage component 272 that serves to absorb and retain liquid bodily waste materials. Suitable known materials for the absorbent core storage component include cellulose fibers in the form of comminuted wood pulp, commonly known as "airfelt", natural or synthetic fibrous materials, and superabsorbent polymers, used either singly or in mixtures and commonly formed into layers or sheets, etc. These absorbent materials may be used separately or in combination. Many known absorbent materials may be used in a discrete form, i.e., in the form of fibers, granules, particles, and the like. Such a discrete form of an absorbent material may be immobilized by an adhesive material that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIG. 25. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer. This separation sheet 292 may extend laterally beyond the side edges 257 of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

In some exemplary embodiments, an absorbent core storage component may include the discrete form of an absorbent material that is immobilized in pockets formed by a layer of a thermoplastic material, such as a hot melt adhesive material, that intermittently contacts and adheres to a substrate sheet, while diverging away from the substrate sheet at the pockets. Absorbent core components having such structures and being suitable for the storage of liquid bodily wastes are described in U.S. Patent Application Publication No. 2004/0162536 dated 19 Aug. 2004 and U.S. Patent Application Publication No. 2004/0167486 dated 26 Aug. 2004. An exemplary absorbent core storage component 272 having such a structure is shown in FIG. 26. In this absorbent core storage component 272, particles 270 of a superabsorbent polymer are contained inside pockets 280 formed by a layer 275 of a thermoplastic material. The absorbent core storage component may include both particles of superabsorbent polymer and airfelt and both materials may be contained inside the pockets formed by the layer of the thermoplastic material. Alternatively, as shown in FIG. 26, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 26, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid waste may pass to the particles to be absorbed by the particles 270 of the superabsorbent polymer.

In FIG. 26, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 26 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet and/or a separate upper covering sheet.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising:
   an absorbent assembly comprising an absorbent core;
   a chassis having a longitudinal axis, a lateral axis, a front waist region having a front waist edge, a back waist region having a back waist edge, a crotch region between the waist regions, laterally opposing left and right side edges extending between the front waist edge and the back waist edge, an exterior surface, and an interior surface to which the absorbent assembly is attached, the chassis comprising a water-impermeable backsheet and laterally opposing side flaps attached to the interior surface adjacent to their longitudinally distal ends, each of the side flaps having a longitudinally extending elastic gathering member attached adjacent to its proximal edge; and
   a support element having a circumferentially extending longitudinally distal edge disposed adjacent to the front waist edge and the back waist edge of the chassis and a longitudinally opposing circumferentially extending longitudinally proximal edge, the support element comprising a front panel attached to the interior surface of the chassis in the front waist region, a back panel attached to the interior surface of the chassis in the back waist region, a left hip panel attached to and extending circumferentially between the left side edge of the chassis in the front waist region and the left side edge of the chassis in the back waist region, such that first and second seams are formed, respectively, and a right hip panel attached to and extending circumferentially between the right side edge of the chassis in the front waist region and the right side edge of the chassis in the back waist region, such that first and second seams are formed, respectively; and
   wherein the left hip panel is seamless between the first and second seams; and wherein the right hip panel is seamless between the third and fourth seams.

2. The disposable diaper of claim 1 wherein the support element includes an elastic material.

3. The disposable diaper of claim 1 wherein the support element includes a skin-contacting layer and an elastic layer laminated to the skin-contacting layer.

4. The disposable diaper of claim 1 wherein the support element comprises a trilaminate including a skin-contacting layer, an exterior cover layer, and an elastic layer sandwiched between the skin-contacting layer and the exterior cover layer.

5. The disposable diaper of claim 4 wherein the trilaminate includes an activated portion in which a ruptured portion of the skin-contacting layer and a ruptured portion of the exterior cover layer provide substantially no resistance to circumferential elongation and the elastic layer provides a circumferential contractive force.

6. The disposable diaper of claim 1 wherein the absorbent assembly is attached to the chassis in a cruciform attachment pattern.

7. The disposable diaper of claim 6 wherein at least a portion of the chassis lying outside the cruciform pattern is laterally extensible.

8. The disposable diaper of claim 1 wherein at least a portion of the chassis in the front waist region or the back waist region is laterally extensible.

9. The disposable diaper of claim 1 wherein the support element comprises an extensible nonwoven.

10. The disposable diaper of claim 9 wherein the extensible nonwoven is elastically extensible.

11. The disposable diaper of claim 1 wherein at least one of the left hip panel and the right hip panel comprises an extensible nonwoven.

12. The disposable diaper of claim 1 wherein at least one of the front panel and the back panel comprises a nonwoven.

13. A disposable diaper comprising:
an absorbent assembly comprising an absorbent core;
a chassis having a longitudinal axis, a lateral axis, a front waist region having a front waist edge, a back waist region having a back waist edge, a crotch region between the waist regions, laterally opposing left and right side edges extending between the front waist edge and the back waist edge, an exterior surface, and an interior surface to which the absorbent assembly is attached in a cruciform attachment pattern, the chassis comprising a water-impermeable backsheet and laterally opposing side flaps attached to the interior surface adjacent to their longitudinally distal ends, each of the side flaps having a longitudinally extending elastic gathering member attached adjacent to its proximal edge; and
a support element including an elastic material and having a circumferentially extending longitudinally distal edge disposed adjacent to the front waist edge and the back waist edge of the chassis and a longitudinally opposing circumferentially extending longitudinally proximal edge, the support element comprising a front panel attached to the interior surface of the chassis in the front waist region, a back panel attached to the interior surface of the chassis in the back waist region, a left hip panel attached to and extending circumferentially between the left side edge of the chassis in the front waist region and the left side edge of the chassis in the back waist region, such that first and second seams are formed, respectively, and a right hip panel attached to and extending circumferentially between the right side edge of the chassis in the front waist region and the right side edge of the chassis in the back waist region, such that third and fourth seams are formed, respectively; and
wherein the left hip panel is seamless between the first and second seams; and wherein the right hip panel is seamless between the third and fourth seams.

14. The disposable diaper of claim 13 wherein at least a portion of the chassis lying outside the cruciform attachment pattern is laterally extensible.

* * * * *